(12) United States Patent
Webster

(10) Patent No.: US 10,493,793 B2
(45) Date of Patent: Dec. 3, 2019

(54) NANOSTRUCTURED SURFACES

(75) Inventor: Thomas J. Webster, Barrington, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 13/639,928

(22) PCT Filed: Apr. 11, 2011

(86) PCT No.: PCT/US2011/031890
§ 371 (c)(1),
(2), (4) Date: Nov. 20, 2012

(87) PCT Pub. No.: WO2011/127463
PCT Pub. Date: Oct. 13, 2011

(65) Prior Publication Data
US 2013/0199539 A1 Aug. 8, 2013

Related U.S. Application Data

(60) Provisional application No. 61/418,838, filed on Dec. 1, 2010, provisional application No. 61/322,366, filed on Apr. 9, 2010.

(51) Int. Cl.
*B44C 1/22* (2006.01)
*A61M 16/04* (2006.01)
*C23F 1/14* (2006.01)

(52) U.S. Cl.
CPC ............ *B44C 1/227* (2013.01); *A61M 16/04* (2013.01); *C23F 1/14* (2013.01); *Y10T 428/24355* (2015.01)

(58) Field of Classification Search
CPC .......... C12N 1/36; C12N 11/00; A61M 16/04; B44C 1/227; C23F 1/14
See application file for complete search history.

(56) References Cited

U.S. PATENT DOCUMENTS

| | | | |
|---|---|---|---|
| 8,632,836 B2 * | 1/2014 | Fredriksson et al. | 427/2.1 |
| 2005/0238685 A1 | 10/2005 | Hektor et al. | |
| 2007/0225434 A1 * | 9/2007 | Lichtenhan | B82Y 30/00 524/730 |
| 2007/0254006 A1 | 11/2007 | Loose et al. | |
| 2008/0020127 A1 | 1/2008 | Whiteford et al. | |
| 2010/0003638 A1 | 1/2010 | Collins et al. | |

FOREIGN PATENT DOCUMENTS

| EP | 1980276 A1 | 10/2008 |
|---|---|---|
| KR | 10-2009-0112686 | 10/2009 |

OTHER PUBLICATIONS

Thapa et al., Biomaterials 24 (2003) 2915-2926.*
Wang et al., Fibers and Polymers 2009, vol. 10, No. 3, 333-337.*
Supplementary European Search Report issued from corresponding EP Patent Application No. 11766855.8, dated Aug. 8, 2013.
Anselme, K., et al.,"The interaction of cells and bacteria with surfaces structured at the nanometre scale," Acta Biomaterialia, Apr. 4, 2010, pp. 3824-3846, vol. 6, No. 10, Elsevier Ltd.
Burgers, Ralf, et al.,"In vivo and in vitro biofilm formation on two different titanium implant surfaces," Clinical Oral Implants Research, Jun. 22, 2009, pp. 156-164, vol. 21, No. 2, John Wiley & Sons.
Cheng, Daniel, et al.,"Formation of nano surfaces on endotracheal tubes using bacterial lipase solutions" Bioengineering Conference, 2009 IEEE 35th Annual Northeast, IEEE, Piscataway NJ, USA, Apr. 3, 2009, pp. 1-2.
Colon, Gabriel, et al.,"Increased osteoblast and decreased *Staphylococcus epidermidis* functions on nanophase ZnO and TiO2," Journal of Biomedical Materials Research Part A, Sep. 1, 2006, pp. 595-604, vol. 78A, No. 3, Wiley Periodicals, Inc.
Komaromy, Andras, et al.,"Influence of surface nanostructure on the extent of colonization and cell viability of *E. coli* and *S. aureus*," Proceedings of Spie, Jan. 1, 2008, pp. 727006-1-727006-8, vol. 7270.
Mitik-Dineva, Natasa, et al.,"Nano-structured surfaces control bacterial attachment," Nanoscience and Nanotechnology, 2008. International Conference on, IEEE, Piscataway, NJ, USA, Feb. 25, 2008, pp. 113-116.
Mitik-Dineva, Natasa, et al., *Escherichia coli, Pseudomonas aeruginosa*, and *Staphylococcus aureus* Attachment Patterns on Glass Surfaces with Nanoscale Roughness, Current Microbiology, Nov. 20, 2008, pp. 268-273, vol. 58, No. 3, Springer Science+Business Media, LLC.
Puckett, Sabrina D., et al.,"The relationship between the nanostructure of titanium surfaces and bacterial attachment," Biomaterials, Feb. 1, 2010, pp. 706-713, vol. 31, No. 4, Elsevier Ltd.
Truong, Vi K., et al.,"The influence of nano-scale surface roughness on bacterial adhesion to ultrafine-grained titanium," Biomaterials, May 1, 2010, pp. 3674-3683, vol. 31, No. 13, Elsevier, Ltd.
Zinger, O., et al."Time-dependent morphology and adhesion of osteoblastic cells on titanium model surfaces featuring scale-resolved topography," Biomaterials, Jun. 1, 2004, pp. 2695-2711, vol. 25, No. 14, Elsevier, Ltd.
Office Action issued for corresponding European Patent Application No. 11766855.8, dated Apr. 14, 2014.
Ban et al., "Surface modification of titanium by etching in concentrated sulfuric acid," 2006. Dental Materials 22, p. 1115-1120.
Zhang et al.,"Cell Response of Titanium Implant With a Roughened Surface Containing Titanium Hydride: An In Vitro Study," 2010. J. Oral Maxillofac. Surg. 68, pp. 1131-1139.

* cited by examiner

*Primary Examiner* — Robert S Cabral
(74) *Attorney, Agent, or Firm* — Adler Pollock & Sheehan P.C.

(57) ABSTRACT

The present invention is directed to methods for inhibiting growth of bacteria and to nanometer scale surfaces having antibacterial properties.

10 Claims, 31 Drawing Sheets

A. Control (Untreated)

B. Nano-structured

A. Control (Untreated)

B. Nano-structured

A. Control (Untreated) Bar = 1 micron

B. Nano-structured Bar = 1 micron

A. Control (Untreated) Bar = 100 nm

B. Nano-structured Bar = 100 nm

C. Control (Untreated)

D. Nano-structured

A. Control (Untreated) Bar = 1 micron

B. Nano-structured Bar = 1 micron

Untreated Surface

Nano-structure

NANOSTRUCTURED SURFACES

RELATED APPLICATION DATA

This application is a National Stage Application under 35 U.S.C. 371 of PCT application PCT/US2011/031890 designating the United States and filed Apr. 11, 2011; which claims the benefit of Provisional patent application No. 61/418,838 and filed Dec. 1, 2010 and Provisional patent application No. 61/322,366 and filed Apr. 9, 2010 each of which are hereby incorporated by reference in their entireties.

FIELD

The present invention relates to the field of nanotechnology and, in particular, to surface geometries on the nanometer scale that are useful to decrease bacterial adhesion. The present invention also relates to the field of implants and/or medical devices having such surface geometries which decrease bacterial adhesion and thereby lower the risk of infection to patients into which the implant or medical device is placed or implanted.

BACKGROUND

The attachment of bacteria to surfaces, sometimes referred to as biofilm formation, often occurs in two major steps. The first is an initial attachment of the bacteria to the surface and the second is a cell-to-cell proliferation to form multilayered bacterial clusters. The initial attachment of the bacteria to the surface is thought to be affected by surface roughness, surface charge, and hydrophobicity. Attachment of bacteria is undesirable on surfaces of devices that are intended to be placed in the body of an individual because of the risk of infection to the individual. Such devices include needles, tubes, implants, medical devices and the like. Attachment of bacteria is further undesirable on surfaces where materials or devices are prepared prior to insertion into an individual. Attachment of bacteria is also undesirable on surfaces where food preparation takes places, as food can become contaminated prior to ingestion. It is desirable to produce a surface where adherence and/or proliferation of bacteria is decreased thereby decreasing the risk of infection.

It is therefore an object of the present invention to create a surface characterized by at least one of surface roughness, surface charge and/or hydrophobicity where the ability of bacteria to adhere to the surface is decreased. It is a further object of the present invention to provide a substrate surface with a surface geometry on the nanometer scale. It is a further object of the present invention to alter the surface of a substrate in a manner to reduce bacterial adhesion and/or proliferation. These and other objects, features, and advantages of the invention or certain embodiments of the invention will be apparent to those skilled in the art from the following disclosure and description of exemplary embodiments.

SUMMARY

Embodiments of the present invention are directed to surfaces of substrates characterized by at least one of surface roughness, surface charge and/or hydrophobicity where the ability of bacteria to adhere, proliferate, and/or colonize to the surface is decreased, inhibited and/or reduced. The surface is referred to herein as being "antibacterial" to the extent that the ability of bacteria to adhere to the surface is decreased thereby reducing the proliferation of bacteria and thereby reducing the risk of infection or illness due to the presence of bacteria. It is to be understood that embodiments of the present invention allow some adherence of bacteria. However, the surface characteristics of the present invention, such as a nanometer scale geometry, reduce the ability of bacteria to adhere to the surface. Further embodiments of the present invention include surface characteristics, such as a nanometer scale geometry, which reduce the ability of bacteria to proliferate.

Embodiments of the present invention are also directed to use of a substrate surface with a surface geometry on the nanometer scale to reduce proliferation of bacteria. Embodiments of the present invention are further directed to methods of altering a surface of a substrate in a manner to reduce bacterial adhesion, proliferation and/or differentiation on the substrate surface. Embodiments of the present invention are further directed to methods of altering a surface of a substrate to create a nanometer scale surface geometry and using the substrate to reduce bacterial proliferation.

Embodiments of the present invention are still further directed to methods of reducing the risk of bacterial infection from the insertion or implantation of devices into an individual. Embodiments of the present invention are even still further directed to methods of reducing the risk of bacterial infection from the use of surfaces that may transmit bacteria during the processing of food or the manufacture of devices or materials intended to be inserted or implanted in an individual. According to the methods, the presence of bacteria is reduced, for example when compared to a surface lacking the nanometer scale surface geometry, thereby reducing the risk of infection or illness due to the presence of bacteria.

According to certain aspects of the present invention, a substrate surface is provided that has a nanometer scale surface roughness. A substrate surface having a nanometer scale surface roughness possesses a higher percentage of atoms at the substrate surface and/or increased portions of surface defects and/or greater numbers of material boundaries at the surface that are influencing protein interactions important for controlling cell functions. A substrate having a nanometer scale surface roughness according to the present invention is characterized by the reduced adhesion and/or proliferation, and/or differentiation of bacterial cells on the surface compared to a substrate lacking the nanometer scale surface roughness. In addition a nanometer scale surface roughness according to the present disclosure decreases inflammation because of an altered surface energy which promotes the adsorption of proteins, such as vitronection and fibronection, that decreases inflammatory cell functions. In addition, a nanometer scale surface roughness according to the present disclosure decreases bacterial functions because of an altered surface energy which promotes the adsorption of proteins, such as vitronection and fibronection, that decreases bacterial functions. In addition a nanometer scale surface roughness according to the present disclosure increases bone formation and growth because of an altered surface energy which promotes the adsorption of proteins, such as vitronection and fibronection, that promote bone cell functions. The substrate of the present invention may also exhibit a surface charge and/or hydrophobicity where the ability of bacteria to adhere to the surface is decreased compared to a surface having a different surface charge and/or hydrophobicity. Accordingly, substrate surfaces of the present invention are useful to reduce the risk of bacterial infection when the substrate is inserted or implanted into an individual. Accordingly, aspects of the present invention contemplate methods of reducing bacterial proliferation, and therefore reducing the risk of bacterial infection or illness, by providing a surface having a nanometer scale surface roughness and/or desirable surface charge and/or desirable hydrophobicity for insertion or implantation into an individual. According to certain aspects of the present invention, a method is provided whereby a substrate surface is altered to create a nanometer scale surface roughness, and then the substrate is inserted or implanted into an individual. According to this aspect, a method is provided to reduce bacterial adhesion, proliferation or differentiation on the surface of the substrate by altering the substrate surface to include a nanometer scale surface roughness and thereby also reduce the risk of bacterial infection or illness when the substrate is introduced or implanted into an individual.

According to particular aspects of the present invention, a method is provided of altering the surface of a substrate by contacting the surface of the substrate with a nano-roughing agent. A nano-roughing agent according to the present disclosure produces a nano-rough surface on the substrate. A nano-rough surface is characterized by a surface morphology having structural features with nanometer dimensions.

According to particular aspects of the present invention, a method is provided of altering the surface of a substrate by contacting the surface of the substrate with a solution of a nano-roughing agent, such as a bacterial lipase and etching the surface of the substrate by the bacterial lipase. According to certain aspects, the bacterial lipase is produced by *Rhisopus arrhisus* or *Candida cilindracea*. According to certain other aspects, the surface of the substrate is contacted with a solution of *Rhisopus arrhisus* or *Candida cilindracea*. According to still other aspects, the etching of the surface with nano-roughing agent produces a nanometer scale surface geometry.

According to other aspects, a method is provided of inhibiting growth of bacteria on the surface of a substrate by providing the surface of the substrate with a nanometer scale surface geometry, contacting the surface with bacteria, and inhibiting adherence and/or growth of the bacteria to the surface. For purposes of the embodiments of the present invention, the step of contacting the surface with bacteria includes bacteria coming into contact with the substrate as would be common when bacteria is transmitted through direct touch or indirect methods such as airborne travel. According to this aspect, bacterial infection in an animal including a human, including the risk of bacterial infection, is reduced when the substrate with the nanostructured surface, such as an endotracheal tube made of PVC or silicone or other like material, is inserted into the animal.

A still further embodiment is provided for a method of reducing growth of bacteria on a surface of a substrate by altering the surface of the substrate to produce a nanometer scale surface geometry by contacting the surface of the substrate with a solution of a nano-roughing agent such as a bacterial lipase and etching the surface of the substrate by the bacterial lipase to produce the nanometer scale surface geometry. According to one embodiment, the bacterial lipase is produced by *Rhisopus arrhisus* or *Candida cilindracea*. According to another embodiment, the surface of the substrate is contacted with a solution of *Rhisopus arrhisus* or *Candida cilindracea*. The substrate, such as an endotracheal tube, may be formed from PVC or silicone or other like materials susceptible to etching by bacterial lipases.

DETAILED DESCRIPTION OF CERTAIN EXEMPLARY EMBODIMENTS

Figure 1A:
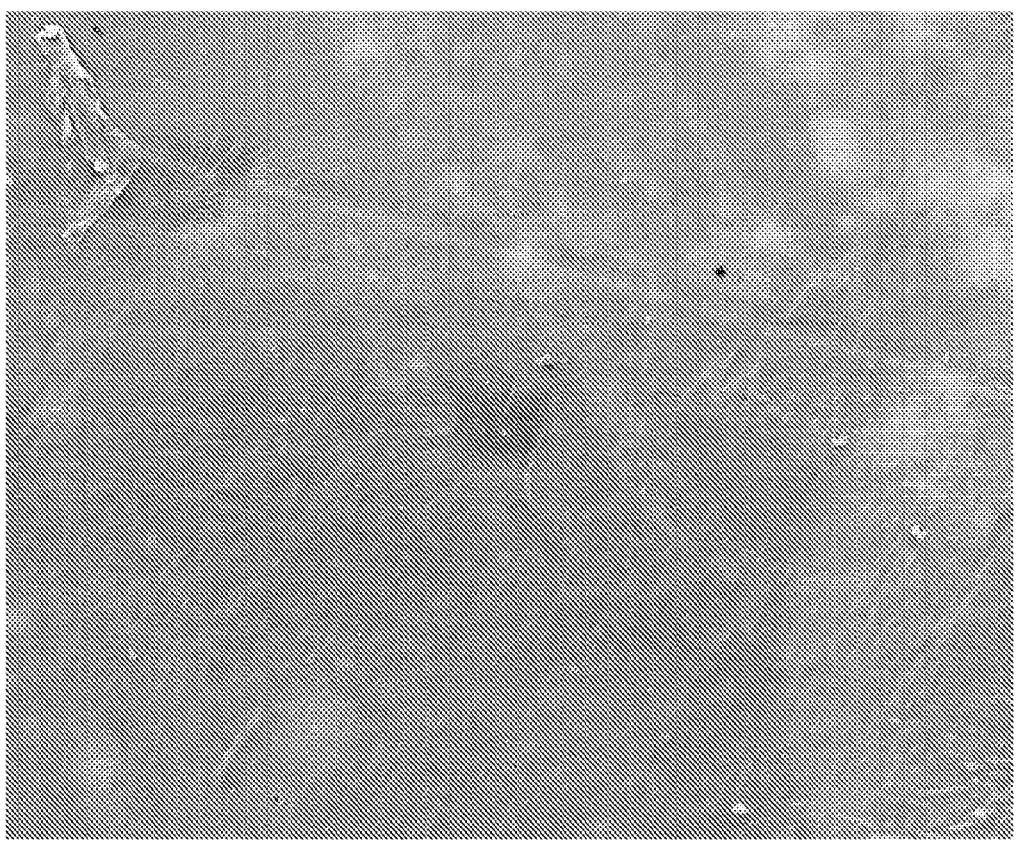
FIG. 1 depicts scanning electron microscope (SEM) images of untreated PVC samples at magnifications of (A) 1 k and (B) 42 k.

Embodiments of the present invention are based on the discovery that surfaces having a nanometer scale geometry, architecture or structure desirably reduce adhesion of bacteria. Since adhesion of bacteria to the surface is reduced, proliferation of bacterial cells is reduced according to embodiments of the present invention and the risk of bacterial infection or illness is also reduced according to embodiments of the present invention.

Bacteria within the scope of the present disclosure includes *Staphylococcus aureus, Staphylococcus epidermis, Pseudomonas aeruginosa*, MRSA, *E. coli*, candida (yeast), *Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium, tuberculosis, Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium, Enterobacteriaceae, Staphylococcus saprophyticus* and the like. The above list is intended to be exemplary and not exhaustive. One of skill in the art will readily be able to identify additional bacteria within the scope of the present disclosure.

Embodiments within the scope of the present invention include substrates that are capable of supporting a nanometer scale geometry, architecture or structure, also referred to herein as "roughness." The surface of the substrates themselves can be altered to remove material from the surface thereby creating a nanometer scale roughness. Alternatively, material may be added to the surface to create a nanometer scale roughness. Still further, the substrate itself can be manufactured such as with a mold to have a surface with a nanometer scale roughness. With each of the above embodiments, the result is a substrate with a surface with a nanometer scale roughness.

Substrates within the scope of the present invention can be fashioned from any material that can support or be altered to provide a nanometer scale roughness. In a particular embodiment, substrates can include any materials susceptible of being degraded, etched or otherwise altered by nano-roughing agents.

Suitable materials include metals, polymers, ceramics, and composites thereof and the like. Metals according to the invention include titanium, aluminum, platinum, niobium, tantalum, tin, nickel, cobalt, chromium, molybdenum, stainless steel, nitinol, Ti6A14V, SiN, CoCrMo, and alloys thereof and the like. The above list is intended to be exemplary and not exhaustive. One of skill in the art will readily be able to identify additional metals and metal alloys within the scope of the present disclosure. Polymers according to the invention include polyvinyl chloride, silicone, polyurethane, polycaprolactone, poly-lactic-co-glycolic acid, poly-lactic acid, poly-glycolic acid, polyethylene, polyethylene glycol, polydimethylsiloxane, polyacrylamide, polypropylene, polystyrene, polyether ether ketone (PEEK), ultra high molecular weight polyethylene (UHMWPE), hydrogels, and composites thereof and the like. The above list is intended to be exemplary and not exhaustive. One of skill in the art will readily be able to identify additional polymers within the scope of the present disclosure. Ceramics according to the invention include alumina, titania, hydroxyapatite, silica, calcium phosphates, bone cements, and composites thereof and the like. The above list is intended to be exemplary and not exhaustive. One of skill in the art will readily be able to identify additional ceramic materials within the scope of the present disclosure. According to a particular embodiment, polymers that are used to fashion devices to be inserted or implanted into an individual, such as poly vinyl chloride and silicon based polymers such as silicones, are useful in the present invention.

Devices within the scope of the present invention that benefit from a reduction of adhesion of bacteria are devices that are intended to be inserted or implanted within an individual. Additional devices include those where food is to be prepared or materials or devices intended to be inserted or implanted are manufactured or staged prior to use. Such devices are commonly found in food processing rooms, kitchens, manufacturing clean rooms, operating rooms and the like. Specific examples of devices intended to be inserted or implanted within an individual include tubes, such as endotracheal tubes, central venous, arterial, and urinary catheters, stents, dialysis tubing, catheters, orthopedic and dental implants, vascular implants, pacemaker leads, neural probes, neural catheters, wound healing devices, skin patches, hernia meshes, spinal implants and the like. Specific examples of devices where food is to be prepared or materials or devices intended to be inserted or implanted are manufactured or staged prior to use such as in an operating room, include tabletops, countertops, trays, plastic cutting boards and the like.

According to certain aspects of the present invention, the surface of the substrate can be altered to produce a nanometer scale surface roughness using one or more nano-roughing agents whether physical or chemical. In this manner, a portion of the substrate surface can be removed by action of a nano-roughing agent. Mechanisms for removing material from a substrate surface include abraiding, degrading, dissolution, etching and the like to produce a nanometer scale surface roughness. Particular methods include contacting the surface of the substrate with a device that will remove material from the substrate surface, such as by friction or abrasion. Alternatively, a liquid or gaseous material can be applied to the surface of the substrate to degrade, dissolve or etch away material from the surface of the substrate to produce a nanometer scale surface roughness. Such treatments are referred to as chemical treatments and include liquid or gaseous materials such as acids, bases, lipases, dichloroethylene and xylene and the like. Surfaces produced by the above methods reduce the growth of bacteria thereon. Exemplary nano-roughing agents include one or more of an acid, a base, an alcohol, a peroxide, isoamyl acetate, dichloromethane, isoamyl acetate with zinc, dichloromethane with zinc, acetic acid, sulfuric acid, nitric acid, perchloric acid, phosphoric acid, hydrochloric acid, chloroform, acetone, ethanol, ammonia, sodium hydroxide, potassium hydroxide, ammonium hydroxide, ammonium fluoride, hydrofluoric acid, triflic acid, hydrogen peroxide, dichloroethylene, xylene and the like and the bacterial lipases previously mentioned. One of skill in the art will readily identify additional nano-roughing agents based on the present disclosure.

According to an exemplary embodiment of the present invention, bacterial lipase solutions are used to produce a nanometer scale surface roughness on a substrate. According to this aspect, substrate surfaces are contacted with lipases, for example from *C. cilindracea* and *R. arrhisus*, in a manner to cause enzymatic degradation of the substrate and nanometer scale features on the surface of the substrate. In this manner, a method is provided to create a nanometer scale surface roughness having antibacterial properties by contacting the surface of a substrate with one or more lipases for a period of time to allow enzymatic degradation of surface materials thereby creating nanometer scale features on the surface of the substrate. In addition to lipases from *C. cilindracea* and *R. arrhisus*, other useful lipases include those from *Candida rugosa*, *Thermus thermophilus*, *Candida Antarctica*, *Aspergillus niger*, *Aspergillus oryzae*, *Aspergillus* sp, *Burkholderia* sp, *Candida utilis*, *Chromobacterium viscosum*, *Mucor javanicus*, *Penicillium roqueforti*, *Pseudomonas cepacia* and the like. Other useful lipases and etchants include phospholipases, sphingomyelinases, hepatic lipase, endothelial lipase, lipoprotein lipase, bile salt dependent lipase, pancreatic lipase, lysosomal lipase, hormone-sensitive lipase, gastric lipase, pancreatic lipase related protein 2, pancreatic lipase related protein 1, lingual lipase and the like.

According to certain aspects of the present invention, the surface of a substrate can be altered in a manner such that material is added to the substrate surface to produce a nanometer scale surface roughness. Material, either the same or different from the material of the substrate surface can be deposited on the surface of the substrate using deposition methods such as vapor deposition well known to those of skill in the art.

According to certain other aspects of the present invention, a nanometer scale surface roughness can be created during the manufacture of the substrate surface such as by use of a mold or other device such as a stamp that can leave a nanometer scale surface roughness imprint onto the surface of the substrate.

According to one aspect of the present invention, the surface of the medical device is modified to include a nanostructured outer surface, that is one characterized by the presence of physical structures having nanometer scale dimensions such as height and/or width. A medical device with such a surface according to the present invention limits, inhibits prevents and/or reduces bacterial adhesion as compared to a device without the nanostructured outer surface.

Examples of such medical devices are those utilizing polyvinyl chloride (PVC) or silicon polymer tubes, such as endotracheal tubes and central venous, arterial, and urinary catheters. Certain embodiments of the present invention are directed to nanostructures on the surface of a medical device that limit adhesion of infection-causing bacteria to the surface of the medical device. According to certain aspects, the nanostructures provide a surface chemistry, surface geometry, surface free energy or condition which limits bacterial adhesion, proliferation and/or differentiation. The nanostructures can take the appearance of etching on the surface of the medical device, for example in the geometry or structural features of lines, points, hills, mounds, valleys, slopes and the like and distances between such geometries and structural features of various nanometer dimensions such as height and/or width and or length and/or depth having dimensions in the range from about 1 nanometer to about 1000 nanometers. For example nanoscale features within the scope of the present invention include those having dimensions between about 10 nanometers to about 900 nanometers, about 100 nanometers to about 500 nanometers, about 1 nanometer to about 100 nanometers, about 10 nanometers to about 50 nanometers, about 1 nanometer to about 10 nanometers, about 1 nanometer to about 5 nanometers, about 10 nanometers to about 100 nanometers, and any ranges in between the above ranges. In one embodiment the lines of etching are spaced about 600 nm from each other. In another embodiment the lines of etching are spaced about 500 nm from each other.

Embodiments of the present invention are also directed to methods of obtaining nanostructured medical devices. According to this aspect of the present invention, one or more nano-roughing agents such as bacterial lipases are selected that will chemically or enzymatically degrade the surface of a medical device when contacted to the surface for a period of time and at a sufficient concentration. One of skill in the art will readily recognize concentrations, time periods and temperatures within the scope of the invention based on the benefit of the disclosure herein. According to one embodiment, the bacterial lipase is *C. cilindracea*. According to another embodiment, the bacterial lipase is *R. arrhisus*.

Embodiments of the present invention are also directed to methods of limiting bacterial adhesion to the surface of a medical device. According to this aspect of the present invention, the nanostructures alter the surface of the medical device. The nanostructured surface provides a different surface roughness than a nanosmooth surface. Without wishing to be bound by theory, it is believed that the nanostructured surface inhibits or prevents the adhesion of bacterial cells to the surface. According to additional embodiments, a nanostructured surface creates a surface charge or hydrophobicity that inhibits, reduces, limits and/or prevents adhesion and or growth of bacterial cells to or on the surface.

Embodiments of the present invention are directed to methods of inhibiting the rate of growth of bacteria over a prolonged period of time. According to one embodiment, a device is provided with or altered to include a nanostructured surface, the nanostructured surface is contacted with bacteria, and the rate of bacterial growth is inhibited or reduced over a prolonged period of time. According to certain embodiments, the rate of bacterial growth is reduced over a prolonged period of time including hours, such as about 4 hours, about 12 hours, about 24 hours, about 72 hours, etc., over a period of days, such as about 1 day, about 2 days, about 3 days, about 4, about 5 days, about 6 days, about 7 days etc., over a period of weeks, such as 1 week, 2 weeks, 3 weeks, 4 weeks, 5, weeks, etc., over a period of months, such as about 1, 2, 3, 4, 5, 6, 7, 8, 9, 10, 11, to about 12 months and over a period of years, such as 1, 2, 3, 4, 5 years etc. It is to be understood that combinations of the above time periods are within the scope of the present invention such as the prolonged period of time could be one week and 3 days, one month and two weeks and four days, one year and three months and one week and two days, etc.

It is to be further understood that embodiments of the present invention include methods of permanently rendering a surface of a substrate resistant to bacterial growth. Such embodiments include the method of providing a substrate with a permanent nanostructured surface, contacting the surface with bacteria, and reducing the adherence and/or growth, and/or proliferation and/or accumulation of bacteria on the surface of the substrate. According to this aspect of the present invention, the methods above for creating a nanostructured surface are performed on a substrate material that retains the nanostructured surface features under normal wear and tear and common environmental and/or physiological conditions. For example, creating a nanostructured surface on a PVC material according to the methods describe herein is considered permanent insofar as the nanostructured surface will remain unaltered at temperatures and environmental conditions which do not cause the PVC material to change its structure. One such set of conditions is physiological conditions and common room temperature environmental conditions. Conditions which could cause the PVC material to alter its structure include coming in contact with heat sufficient to melt and/or destroy the PVC and/or solvents which could dissolve the PVC material. Under this embodiment, the term "permanent" includes the useful life of the substrate including the nanostructured surface. So long as the nanostructured surface is capable of coming into contact with bacteria, and the surface retains its nanometer scale surface structural features, the surface is permanently rendered resistant to bacterial growth.

An additional embodiment of the present invention includes a method of improving resistance of a substrate to bacterial growth including providing a substrate surface with features having nanometer scale dimensions, i.e. a nanostructured surface, contacting the surface with bacteria, reducing the growth of bacteria, removing bacterial growth, and repeating the steps of contacting, reducing and removing in whole or in part any numbered of desired times. According to this embodiment, the substrate having the nanostructured surface is reusable in methods of reducing growth of bacteria or otherwise reducing the rate of growth of bacteria. The step of removing is accomplished by common wiping or cleaning or sterilizing techniques known to those of skill in the art.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, and accompanying claims.

EXAMPLES

The following examples are specific embodiments of the present invention but are not intended to limit it.

Example 1

Formation of Nanostructured Surfaces on Endotracheal Tubes Using *R. arrhisus*

0.1% and 0.5% mass solutions of *Rhisopus arrhisus* were each prepared in potassium phosphate buffer at a pH of 7.4. 10 mL of each solution was then placed in a glass Petri dish with a sample of a polyvinyl chloride (PVC) endotracheal tube (1 cm×1 cm). The PVC sample was left at 37° C. for 24 hours. The sample was then removed, washed with distilled water, and returned to the Petri dish with fresh solution for another 24 hours. The enzymatic degradation of the PVC was measured for 48 hours. The activity of *R. arrhisus* was measured to be 10.5 U/g. One unit is defined to be the amount of enzyme that catalyzed the release of 1 µmol of oleic acid per minute.

Figure 1B:
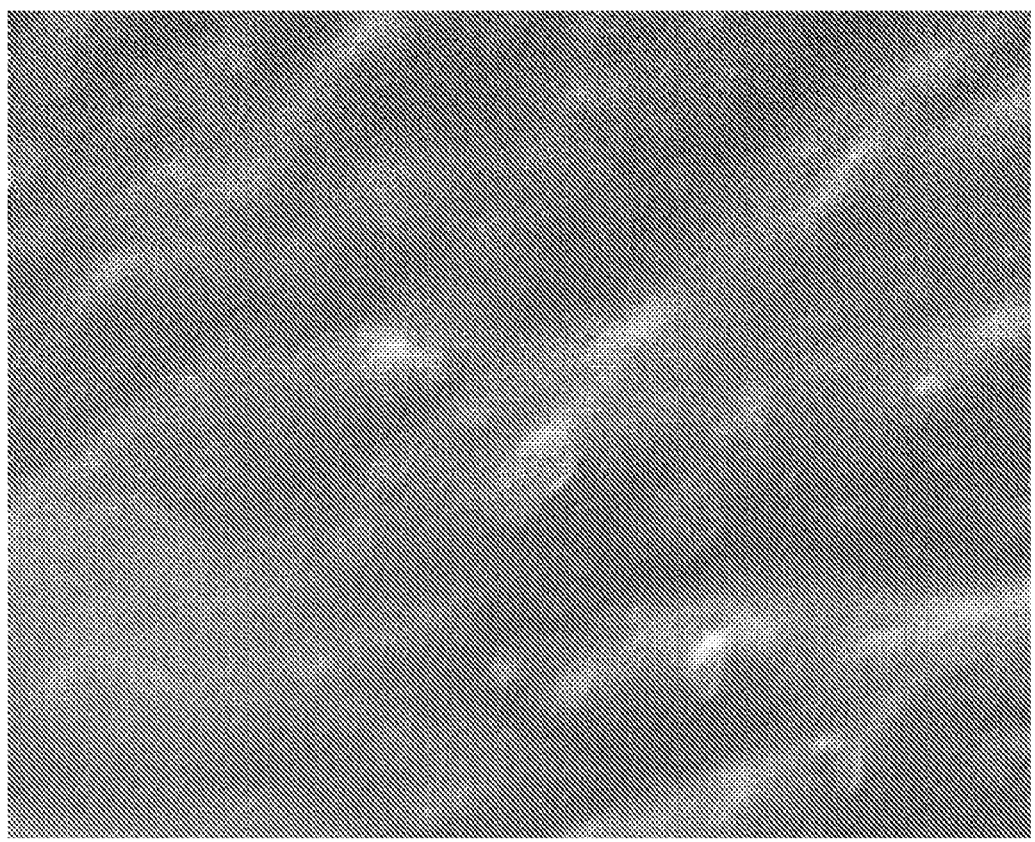
Figure 2A:
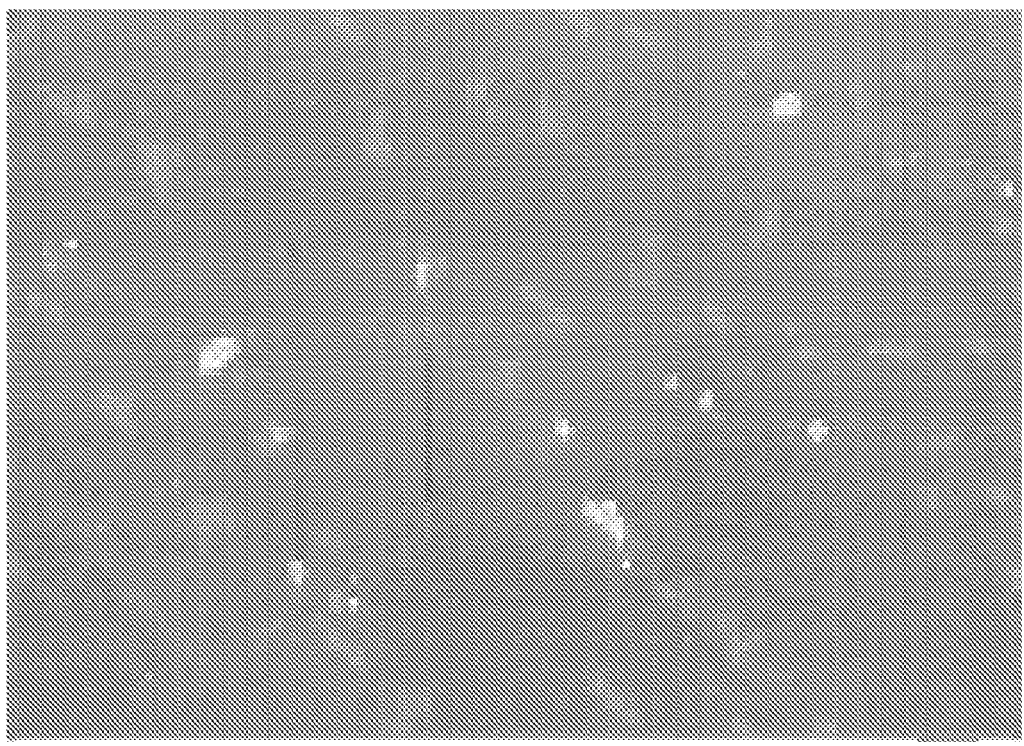
FIG. 2 depicts SEM images at magnification of 20 k of PVC treated after 24 hours with (A) 0.5% solution of *R. arrhisus* and (B) 0.5% solution of *C. cilindracea*.
Figure 4A:
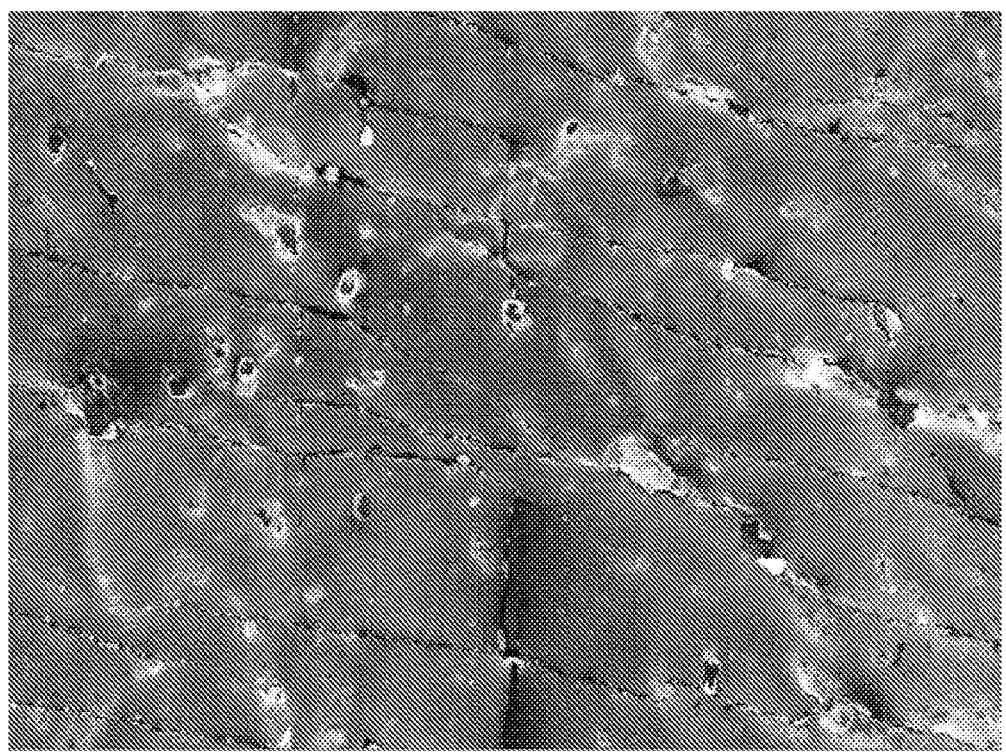
FIG. 4 depicts SEM images of PVC treated after 48 hrs with 0.1% *R. arrhisus* solution at magnification of (A) 10 k and (B) 42 k and with 0.5% *R. arrhisus* solution at magnification of (C) 20 k and (D) 42 k.
Figure 4B:
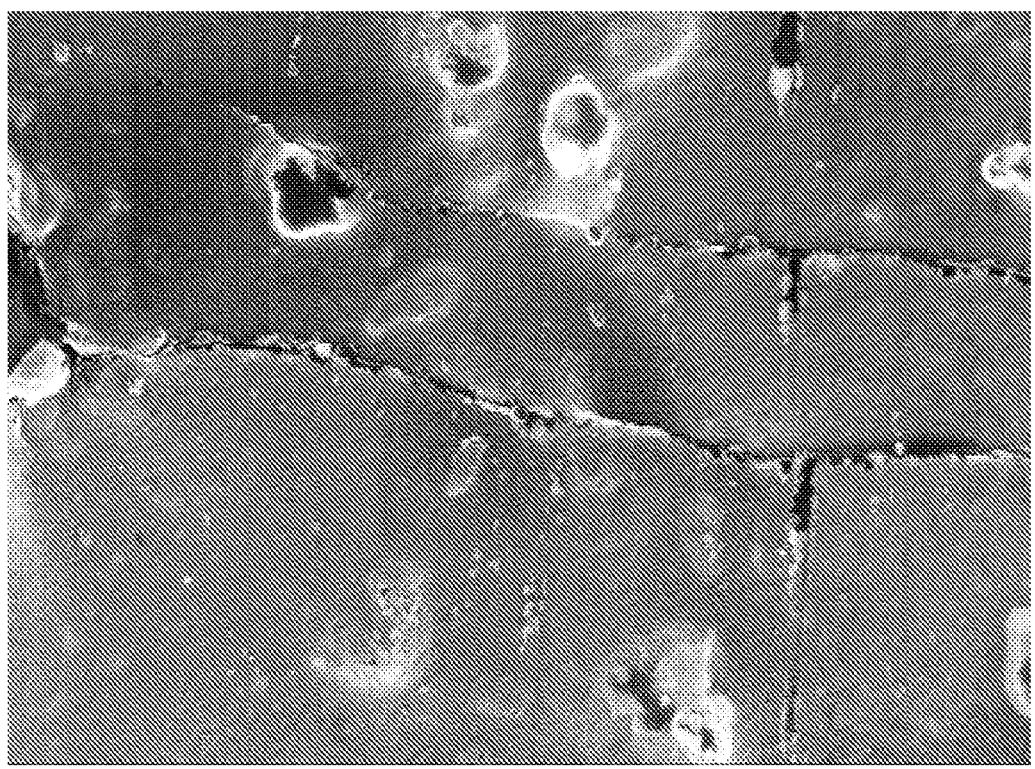
Figure 4C:
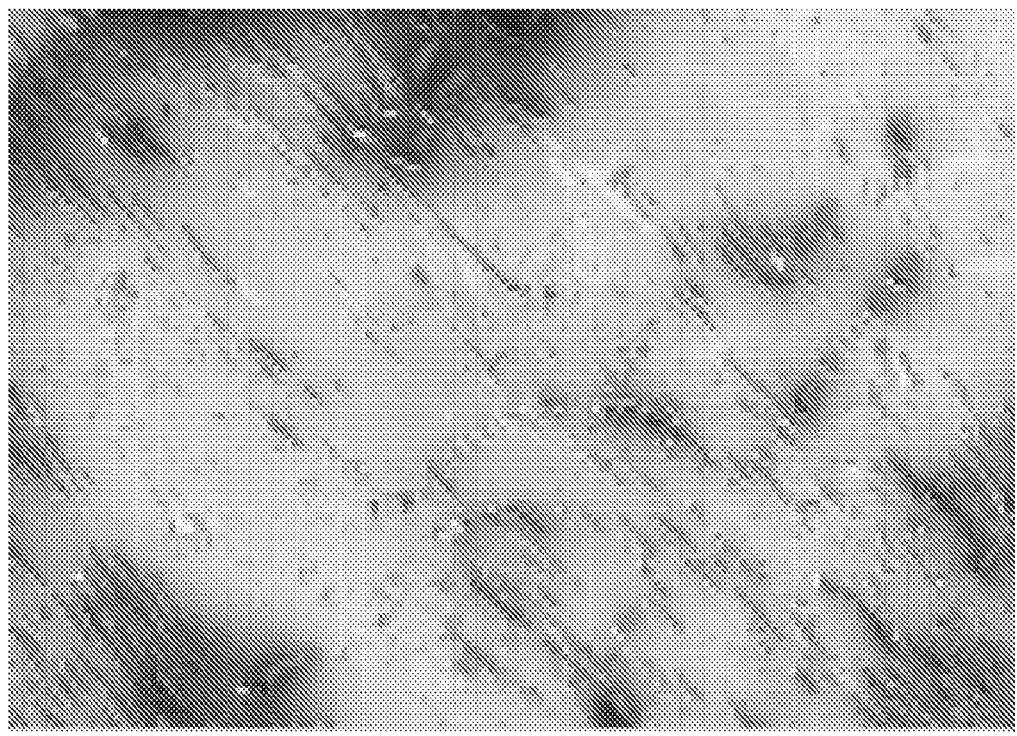
Figure 4D:
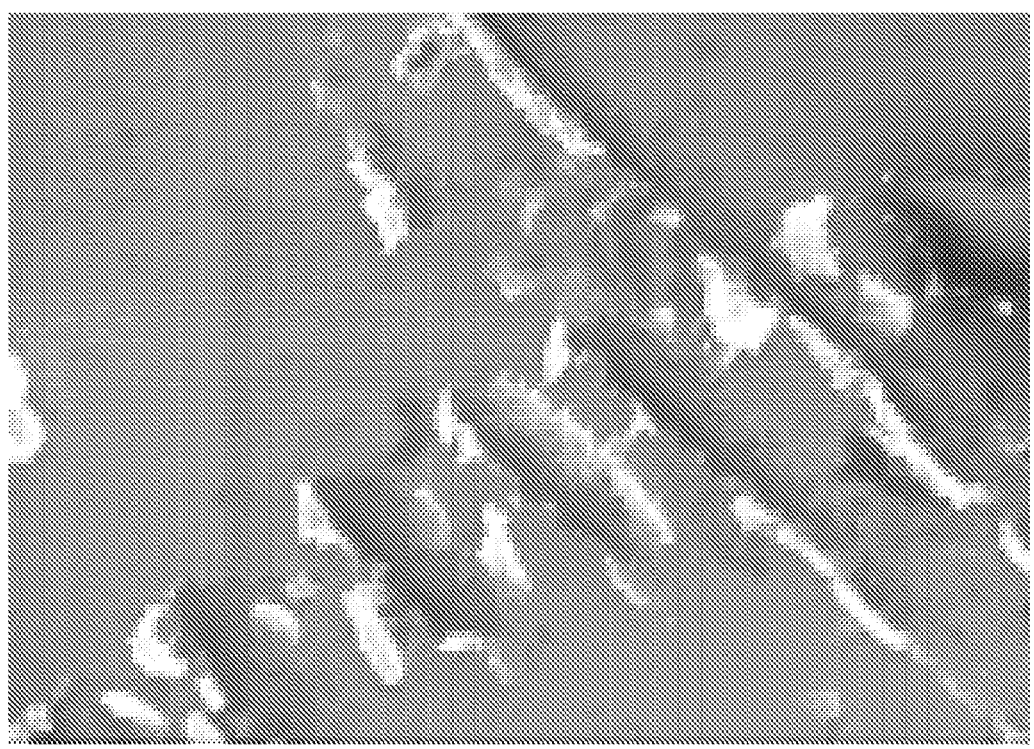
Figure 5:
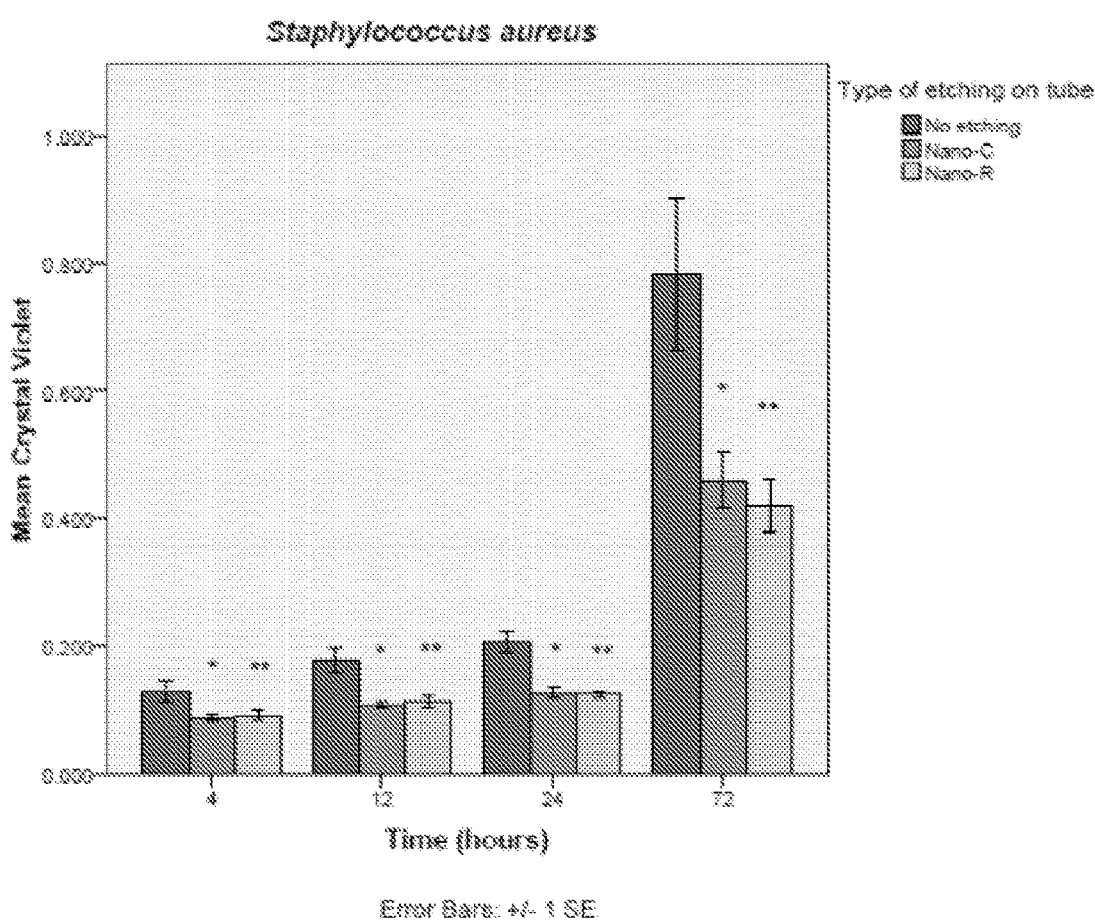
FIG. 5 is a graph depicting bacteria growth of *Staphylococcus aureus* on untreated PVC (blue bar), PVC treated with *C. cilindracea* (green bar) and PVC treated with *R. arrhisus* (tan bar).
Figure 6A:
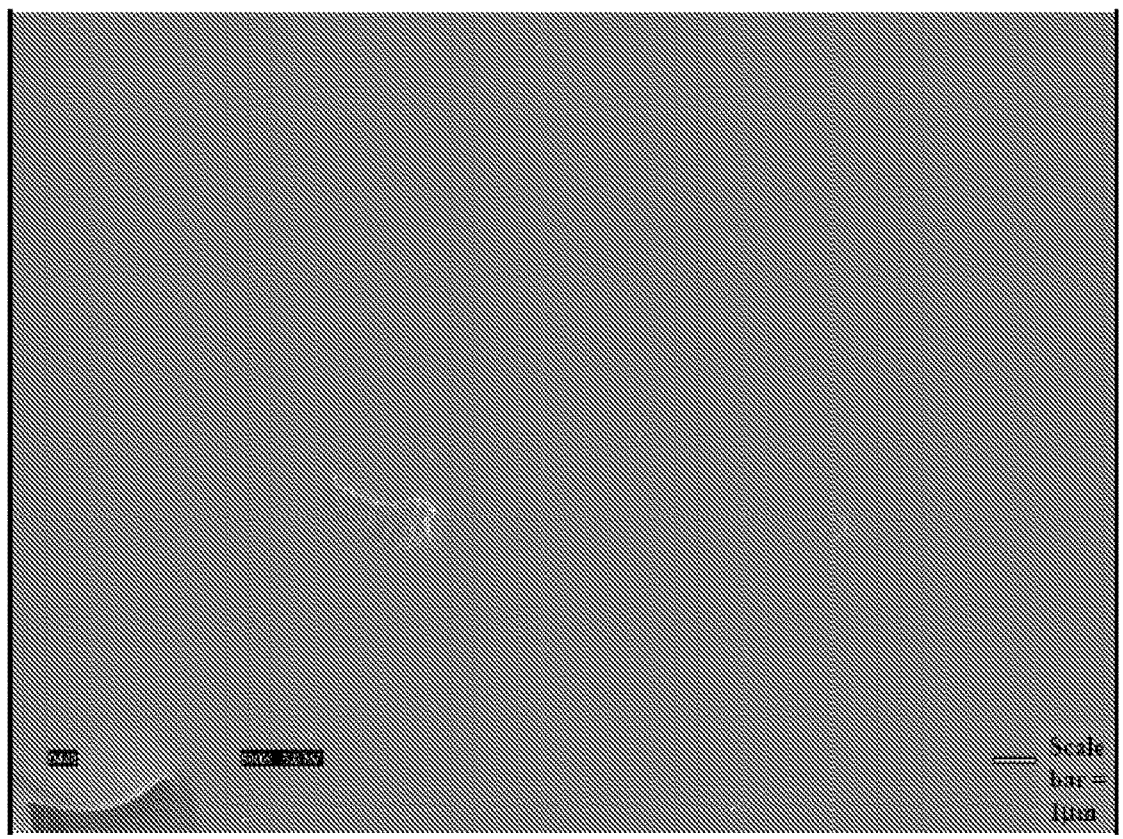
FIG. 6 depicts SEM images of untreated PVC treated (A, 20 k magnification) and PVC treated with *R. arrhisus* solution (B, 20 k magnification).
Figure 6B:
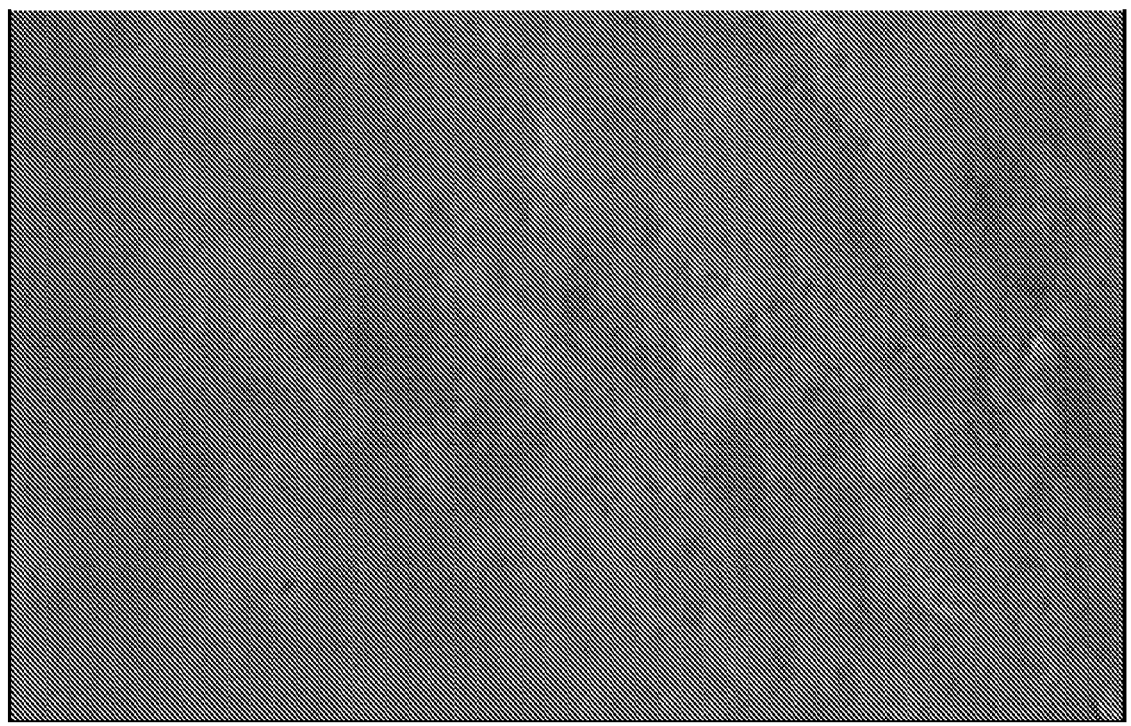

The samples were observed at the 24 hour and 48 hour mark using a scanning electron microscope (SEM). As a control, SEM micrographs of untreated PVC samples were taken at magnifications of 1 k (FIG. 1*a*) and 42 k (FIG. 1*b*). After 24 hours of soaking in a 0.5% solution of *R. arrhisus*, nano features could be seen on the treated PVC sample as shown in FIG. 2*a* at magnification of 20 k. After 48 hours of soaking in a 0.1% *R. arrhisus* solution, nano features could be seen on the treated PVC sample as shown in FIG. 4*a* (10 k magnification) and FIG. 4*b* (42 k magnification). After 48 hours of soaking in a 0.5% *R. arrhisus* solution, nano features could be seen on the treated PVC sample as shown in FIG. 4*c* (20 k magnification) and FIG. 4*d* (42 k magnification). Visible nano features with clear etching of the surface was demonstrated. The etching produced substantially uniform lines spaced about 500 nm apart. In a separate experiment, SEM micrographs were taken of untreated PVC and PVC treated with *R. arrhisus* at 0.5% for 72 hours showing the scale of features produced by the treatment. As shown in FIGS. 6*a* and 6*b*, the treatment with *R. arrhisus* produced nanometer scale features.

Example 2

Formation of Nanostructured Surfaces on Endotracheal Tubes Using *C. cilindracea*

0.1% and 0.5% mass solutions of *Candida cilindracea* were each prepared in potassium phosphate buffer at a pH of 7.4. 10 mL of each solution was then placed in a glass Petri dish with a sample of a polyvinyl chloride (PVC) endotracheal tube (1 cm×1 cm). The PVC sample was left at 37° C. for 24 hours. The sample was then removed, washed with distilled water, and returned to the Petri dish with fresh solution for another 24 hours. The enzymatic degradation of the PVC was measured for 48 hours. The activity of *C. cilindracea* was measured to be 7.29 U/g.

Figure 2B:
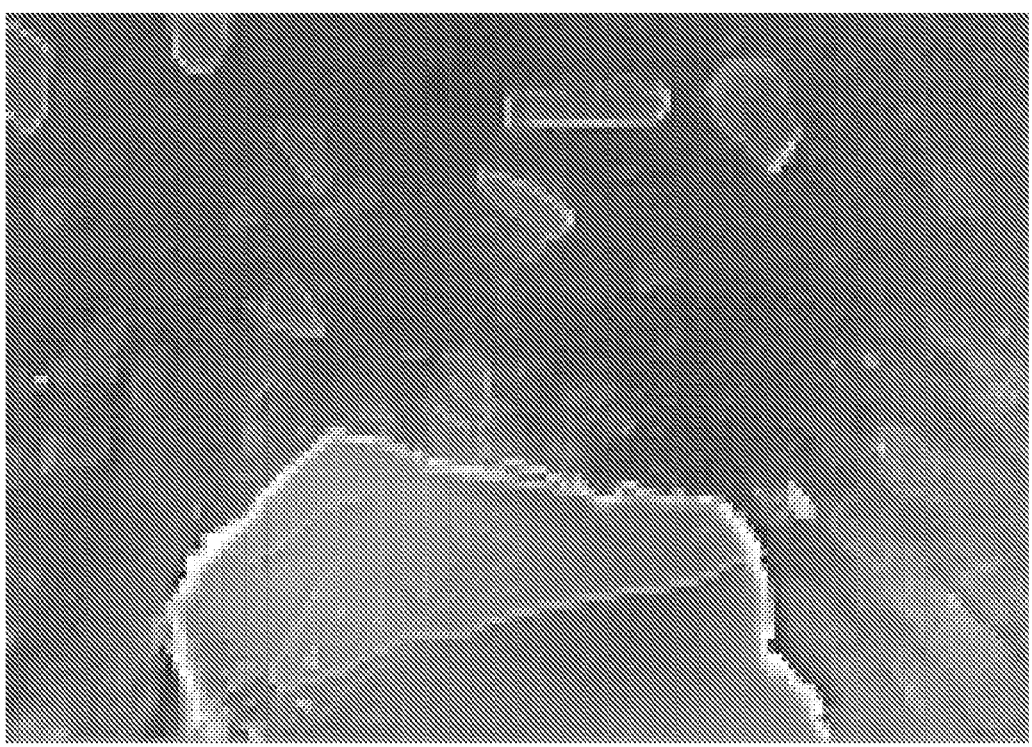
Figure 3A:
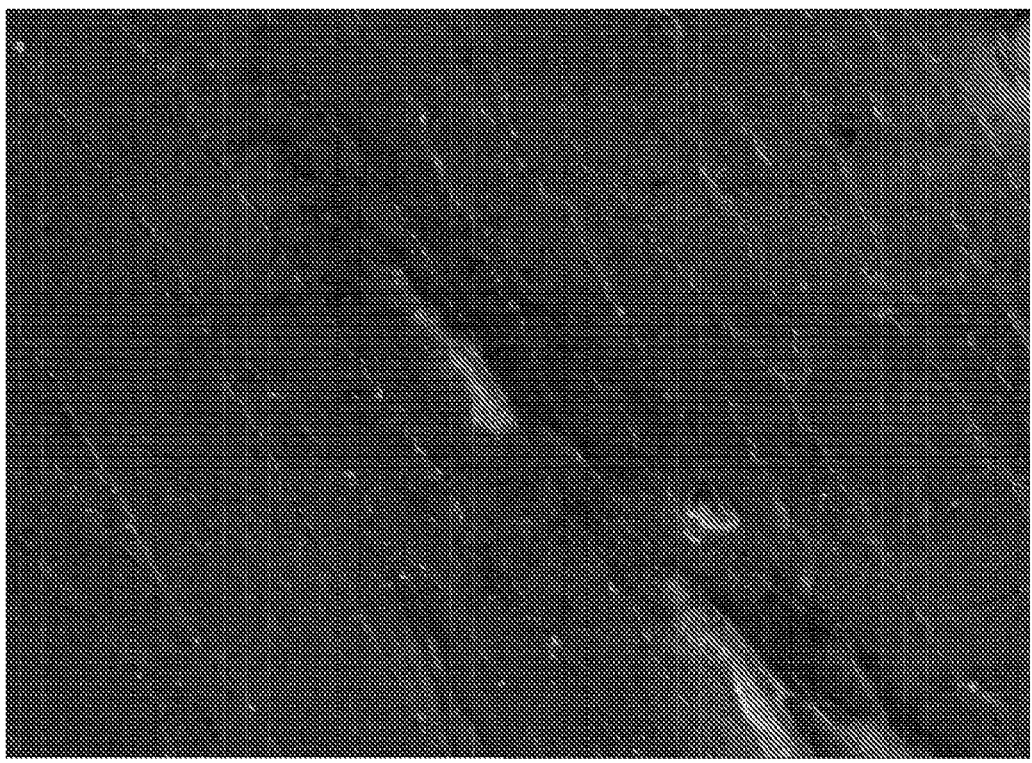
FIG. 3 depicts SEM images of PVC treated with 0.1% *C. cilindracea* solution after 48 hrs at magnification of (A) 5 k and (B) 42 k.
Figure 3B:
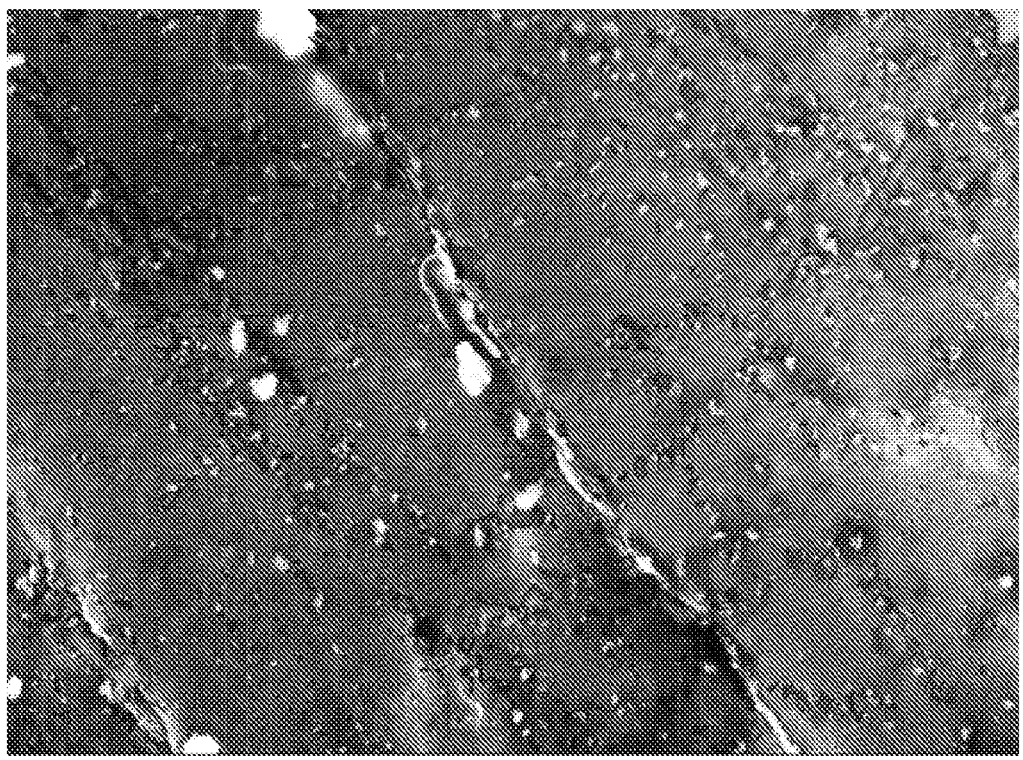

The samples were observed at the 24 hour and 48 hour mark using a scanning electron microscope (SEM). After 24 hours of soaking in a 0.5% solution of *C. cilindracea*, nano features could be seen on the treated PVC sample as shown in FIG. 2b at magnification of 20 k. After 48 hours of soaking in a 0.1% *C. cilindracea* solution, nano features could be seen on the treated PVC sample as shown in FIG. 3a (5 k magnification) and FIG. 3b (42 k magnification). Visible nano features with clear etching of the surface was demonstrated. The etching produced substantially uniform lines spaced about 600 nm apart. As shown in the SEMs, the features having nanometer scale dimensions have the shapes of lines, dots, spots, hills, points, mounds, valleys, and slopes. According to one embodiment shown, the features are in the shape of elongated features such as lines, broken lines, spots in series forming a lines, wherein one or more of the elongated features are substantially parallel to one another and are of a substantially similar height and width.

Example 3

Decreased *Staphylococcus aureus* Growth on Nanostructured Surfaces

*Staphylococcus aureus* was grown on nanostructured PVC that had been treated with *R. arrhisus* and *C. cilindracea* in the manner described above, as well as on a control with no etching. Bacteria were cultured in trypic soy broth under standard biological conditions, specifically under a 37° C., humidified, 5% $CO_2$/95% air environment. The samples were stained with Crystal Violet and the growth of bacteria was measured at 4 hours, 12 hours, 24 hours, and 72 hours. A substantial decrease in bacterial growth and/or reduction in the rate of bacterial growth or proliferation was seen between the untreated sample and the treated samples over time. According to methods of the present invention, a substantial reduction in growth of bacteria is achieved after 72 hours. Given the permanent nanostructured surface of the substrate used in this experiment and the demonstrated reduction in bacterial growth, one of skill will understand that the reduction in the growth or rate of growth will continue even longer and for the useful life of the substrate. One of skill will further understand that the surface of the substrate has been rendered permanently resistant to bacterial growth, and that the capability of the substrate to resist bacterial growth is enhanced by removing bacteria that have accumulated on the surface of the substrate. One of skill will further understand based on this example that other etchants as described above can be used to produce a surface of a substrate having nanometer scale features. Surfaces composed of one or more materials as described above other than PVC are useful in the present invention. The substrate having the nanosurface thereon is any of the substrates described above where, for example, reduced or inhibited bacterial growth is desired. According to the present invention, substrates such as endotracheal tubes, can be altered to include a surface having nanometer scale features and the endotracheal tube can be used in the methods of reducing growth or rate of growth of bacteria or otherwise reducing the risk of bacterial infection that often accompanies introducing such a substrate into a patent.

Example 4

Formation of Nano-Structured Surface on Polypropylene

Polypropylene substrate samples were treated in either isoamyl acetate or dichloromethane for 42 hours using a method similar to that described in Example 1. For some of the samples, ZnCl was added to either the isoamyl acetate or dichloromethane to introduce Zn particles onto the substrate. Upon complete of the treatment, the samples were removed and rinsed three times in distilled water.

Example 5

Decreased Inflammatory Cell Functions

Figure 7:
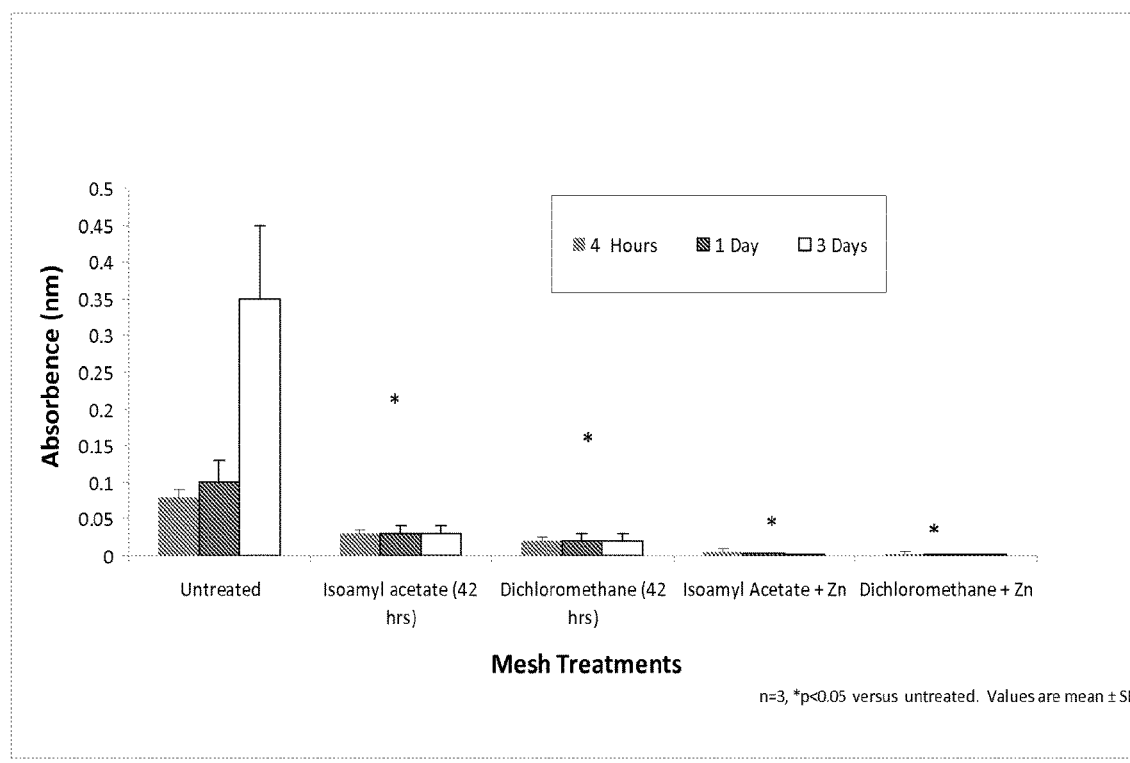
FIG. 7 is a graph of macrophage density for polypropylene substrates that are untreated, treated with isoamyl acetate, treated with dichloromethane, treated with isoamylacetate and zinc chloride and treated with dichloromethane and zinc. Nanostructured polypropylene (without LPS) surfaces had less macrophage density compared to the untreated surface.

Macrophages (ATCC) were seeded at 2500 cells/$cm^2$ onto the substrates of interest in standard cell culture media for 4 hours and 1 and 5 days under standard cell culture conditions. At the end of the prescribed time period, adherent cells were determine using standard MTT assays. Experiments were repeated in triplicate at least three times each. As shown in FIG. 7, nanostructured polypropylene (without lipopolysaccharide) exhibited less macrophage density.

Figure 8:
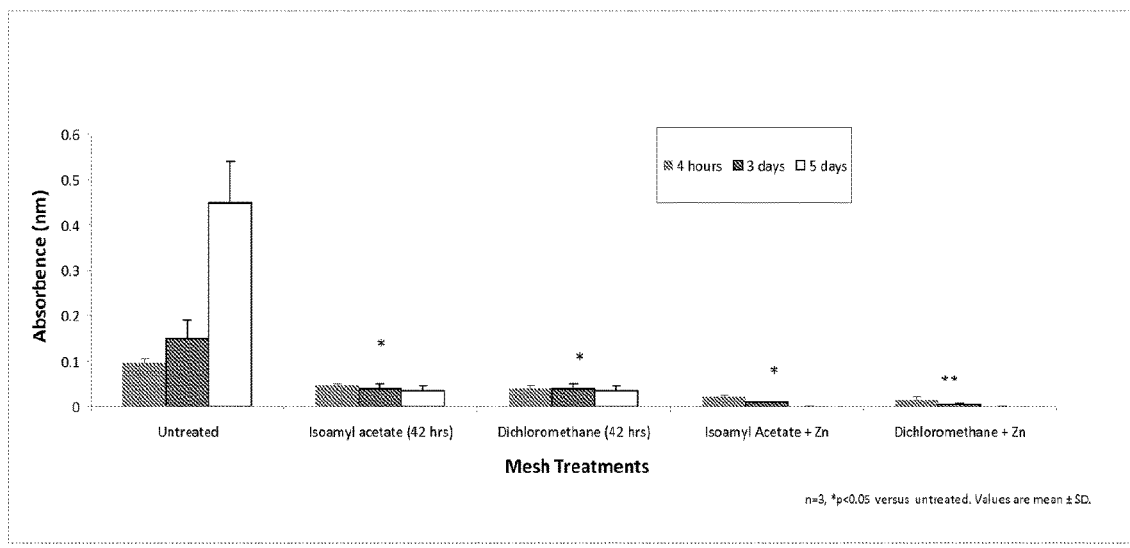
FIG. 8 is a graph of macrophage density for polypropylene substrates that are untreated, treated with isoamyl acetate, treated with dichloromethane, treated with isoamylacetate and zinc chloride and treated with dichloromethane and zinc. Nanostructured polypropylene (with LPS) surfaces had less macrophage density compared to the untreated surface.

Macrophage experiments were conducted as described above. As shown in FIG. 8, nanostructured polypropylene (with lipopolysaccharide) exhibited less macrophage density.

Example 6

Decreased Bacteria Functions

Figure 9:
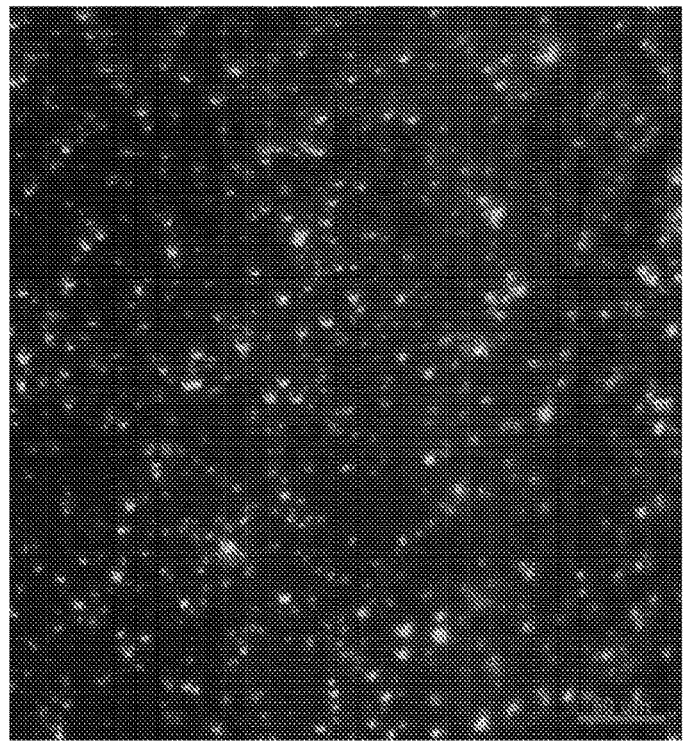
FIG. 9 are images showing the relative amount of bacteria on an untreated polyethyl ethyl ketone substrate (A) and a polyethyl ethyl ketone substrate with a nano-rough or nano-structured surface (B). The polyethyl ethyl ketone substrate with a nano-rough or nano-structured surface had lower amounts of *Staphylococcus epidermis* bacteria.
Figure 9:
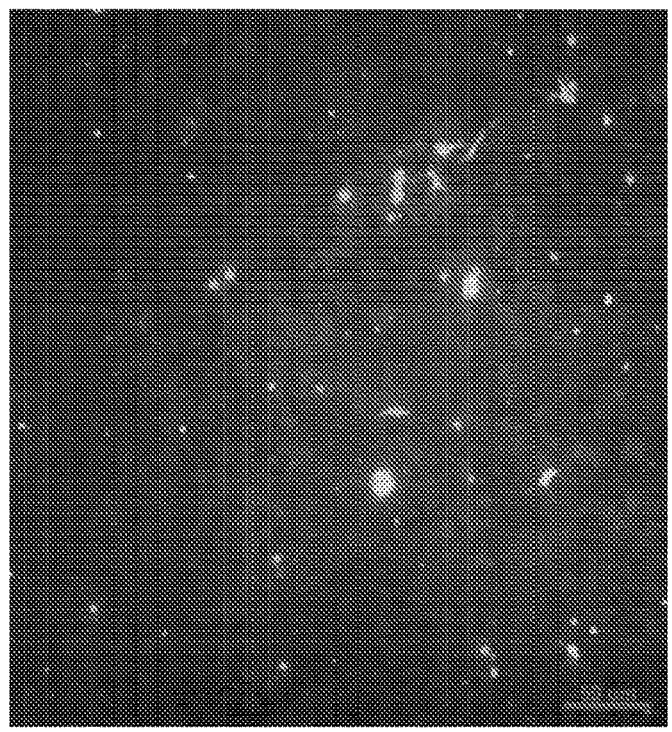

As shown in FIG. 9, a nanostructured surface of poly ether ether ketone (PEEK) demonstrated antibacterial properties against *Staph. epidermidis* using a method similar to that described in Example 3.

Figure 10:
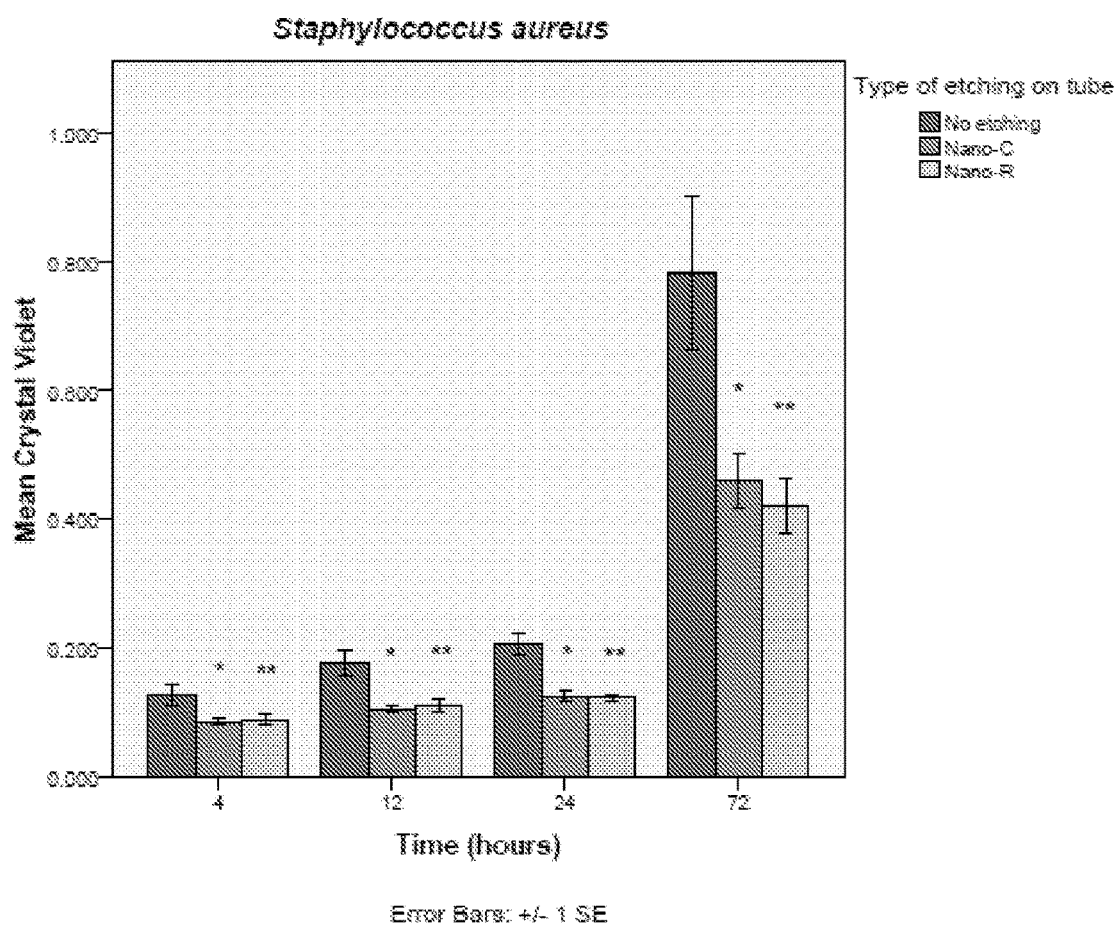
FIG. 10 is a graph depicting relative amounts of *Staphylococcus aureus* bacteria for an untreated polyvinyl chloride substrate from an endotracheal tube, a polyvinyl chloride substrate from an endotracheal tube treated with *Candida cilindracea* (Nano-C) and a polyvinyl chloride substrate from an endotracheal tube treated with *Rhisopus arrhisus* (Nano-R) to create nano-scale features. The polyvinyl chloride with a nano-rough or nano-structured surface had lower amounts of *Staphylococcus aureus* bacteria.

As shown in FIG. 10, a nanostructured surface of PVC demonstrated antibacterial properties against *Staphylococcus aureus* using substrates treated with either *Rhisopus arrhisus* or *Candida cilindracea*.

Figure 11:
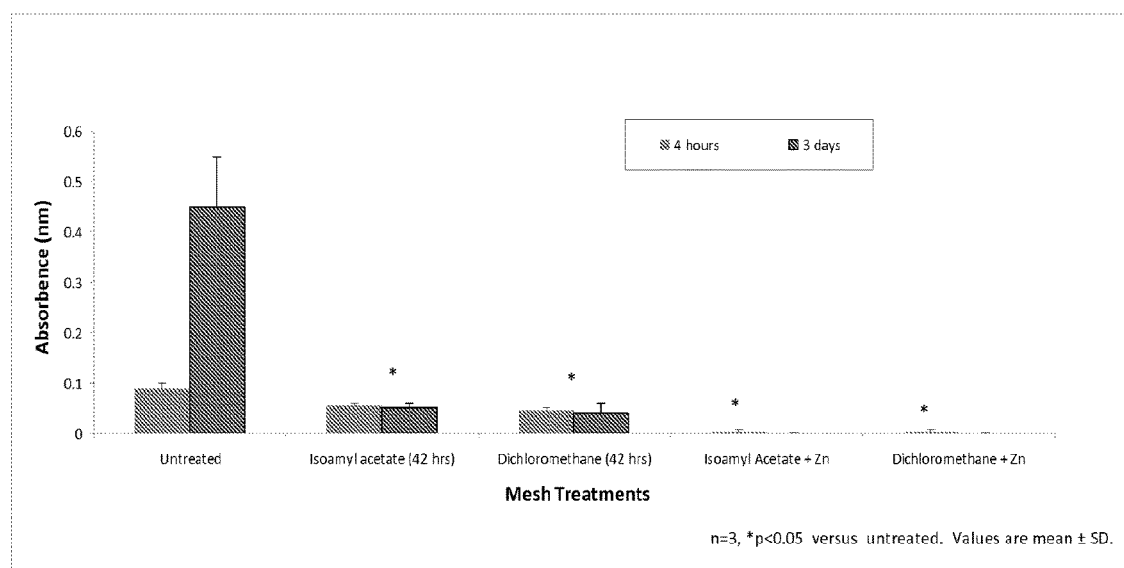
FIG. 11 is a graph of *Staphylococcus epidermis* colonization for polypropylene substrates that are untreated, treated with isoamyl acetate, treated with dichloromethane, treated with isoamylacetate and zinc chloride and treated with dichloromethane and zinc. Nanostructured polypropylene had less *Staphylococcus epidermis* colonization compared to the untreated surface.

As shown in FIG. 11, a nanostructured surface of polypropylene demonstrated antibacterial properties against *Staph. epidermidis* colonization.

Example 7

Enhanced Osteoblast Calcium Deposition on Nano-Structured PEEK

Figure 12:
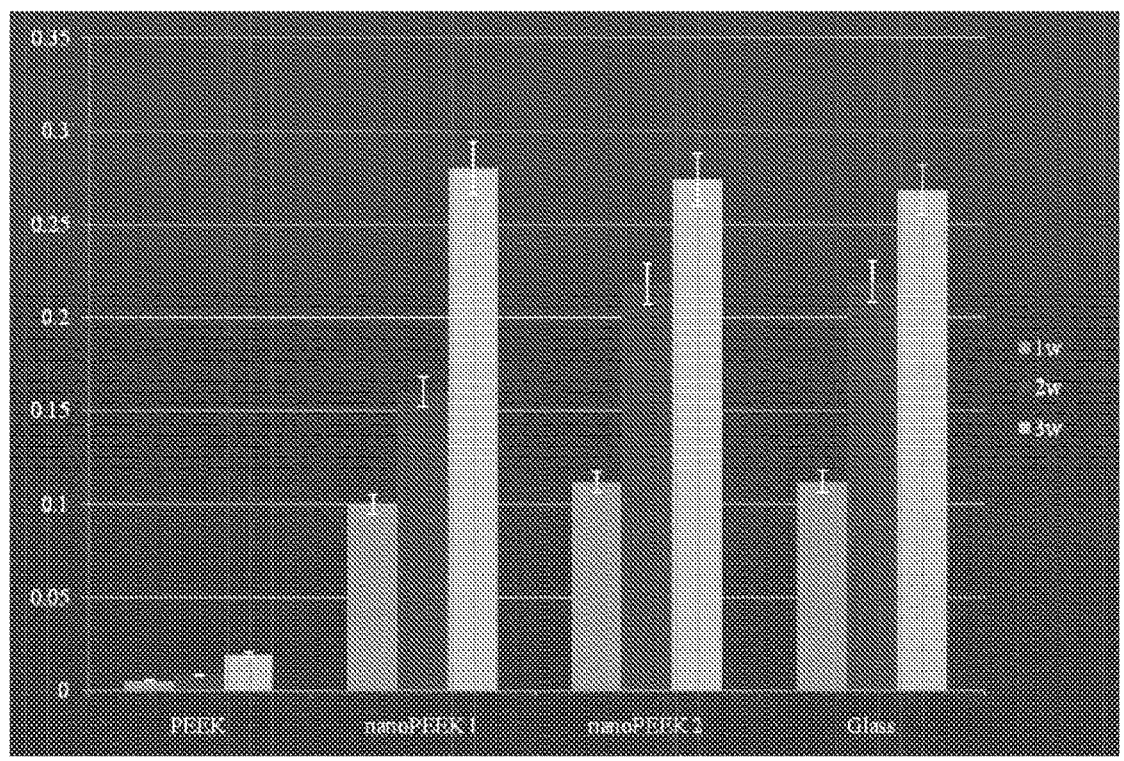
FIG. 12 is a graph of calcium deposition in micrograms/cm$^2$ for untreated polyethyl ethyl ketone (PEEK), treated polyetherether ketone (nanoPEEK1), treated polyetherether ketone (nanoPEEK2) and glass. The treated polyetherether ketone had enhanced osteoblast calcium deposition compared to untreated polyetherether ketone and osteoblast calcium deposition similar to glass.

Osteoblasts (ATCC) were seeded on the substrates of interest at 40,000 cells/$cm^2$ and were cultured in standard cell culture media for 1, 2, and 3 weeks under standard cell culture conditions with the media changed every other day. At the end of the prescribed time period, samples were rinsed in saline solution and soaked in HCl to dissolve calcium deposited by the osteoblasts in the extracellular matrix. The calcium containing supernatants were then analyzed using the Calcium Assay (Sigma). Experiments were completed in triplicate at least three times each. As shown in FIG. 12, nano-structured PEEK demonstrated enhanced osteoblast calcium deposition.

Example 8

Nanostructured Surface Materials

Figure 13:
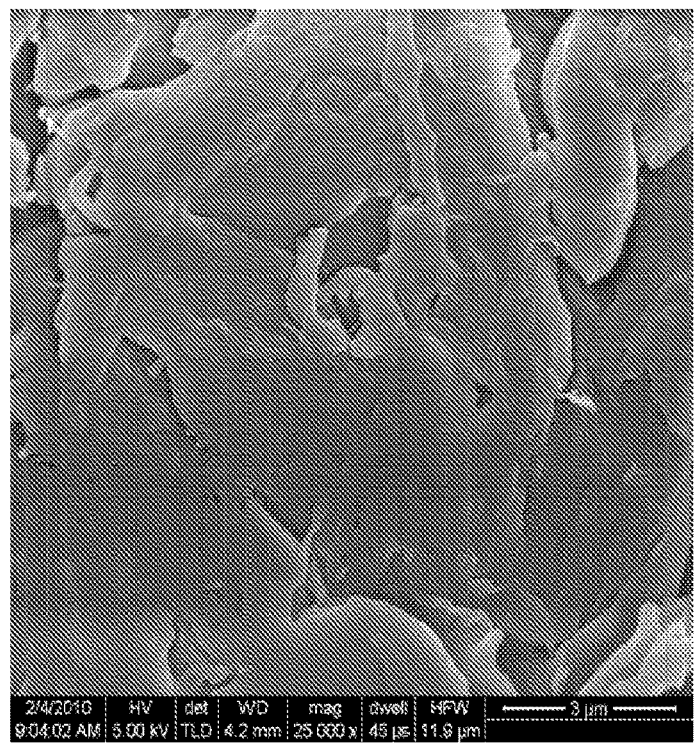
FIG. 13 is an image of the surface morphology of untreated polyetherether ketone (A) and nano-structured polyetherether ketone (B).
Figure 13:
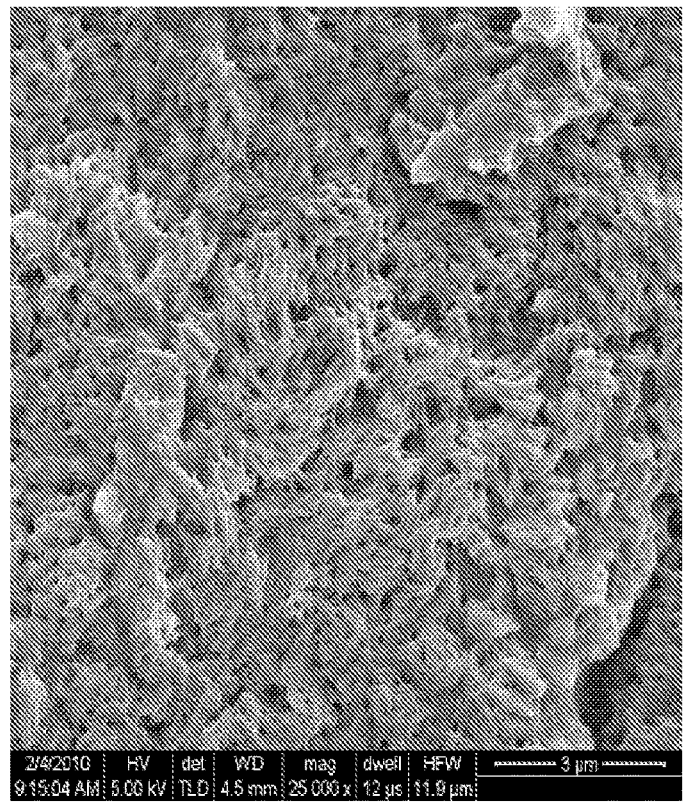

As shown in the SEM image of FIG. 13, the control (untreated) surface of polyetherether ketone (A) is smooth relative to the nano-rough surface morphology of polyetherether ketone (B) treated using a protocol similar to that described in Example 1.

Figure 14:
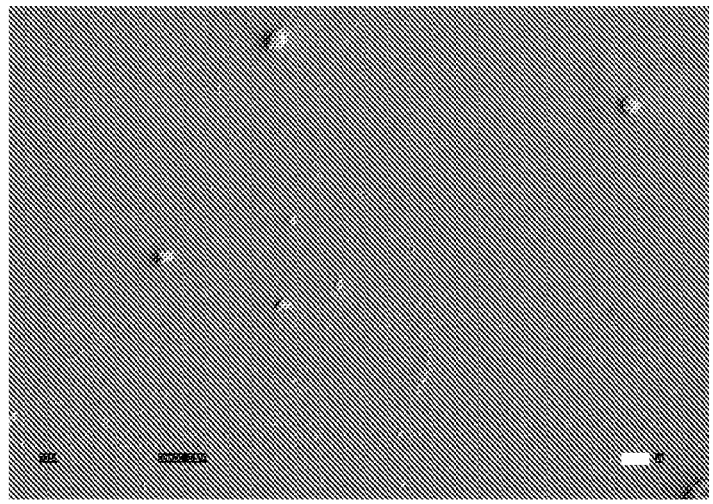
FIG. 14 is an image of the surface morphology of untreated polyglycolic acid (A) and nano-structured polyglycolic acid (B).
Figure 14:
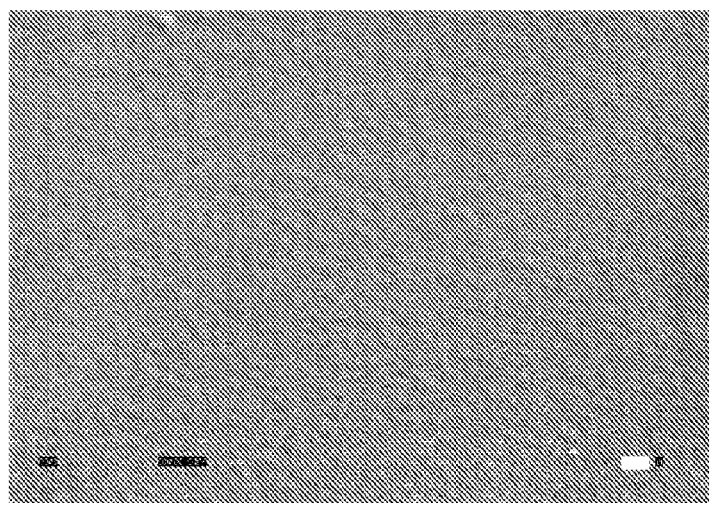

As shown in the SEM image of FIG. 14, the control (untreated) surface of polyglycolic acid (A) is smooth relative to the nano-rough surface morphology of polyglycolic acid (B) treated using a protocol similar to that described in Example 1.

Figure 15:
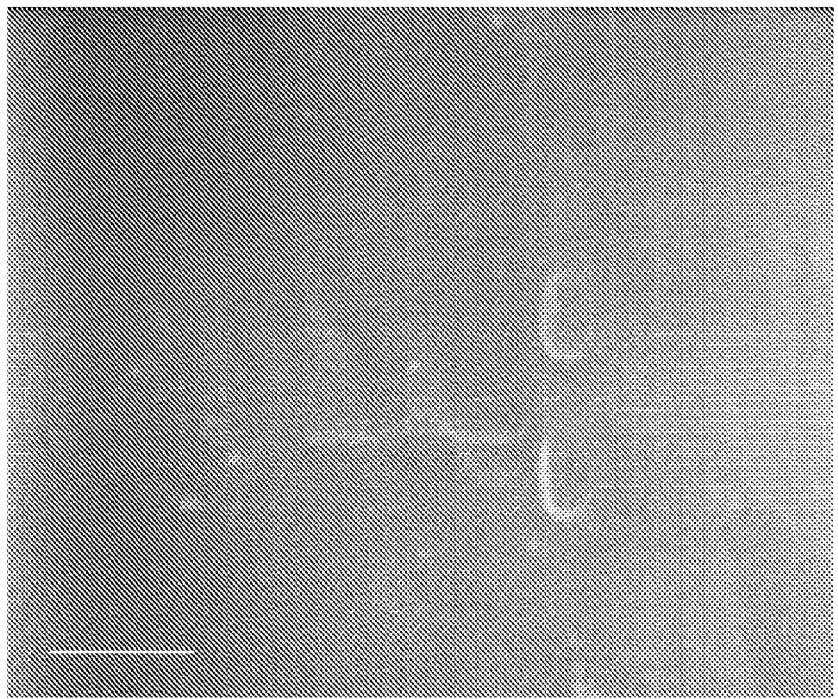
FIG. 15 is an image of the surface morphology of untreated polypropylene (A), nano-structured polypropylene (B), untreated polypropylene mesh fibers (C) and nano-structured polypropylene mesh fibers (D).
Figure 15:
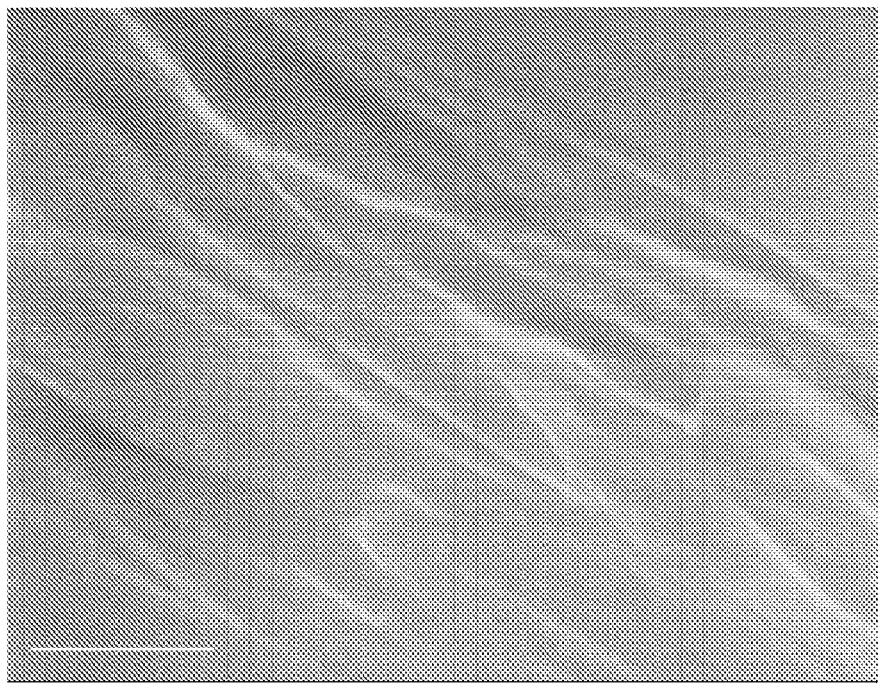
Figure 15:
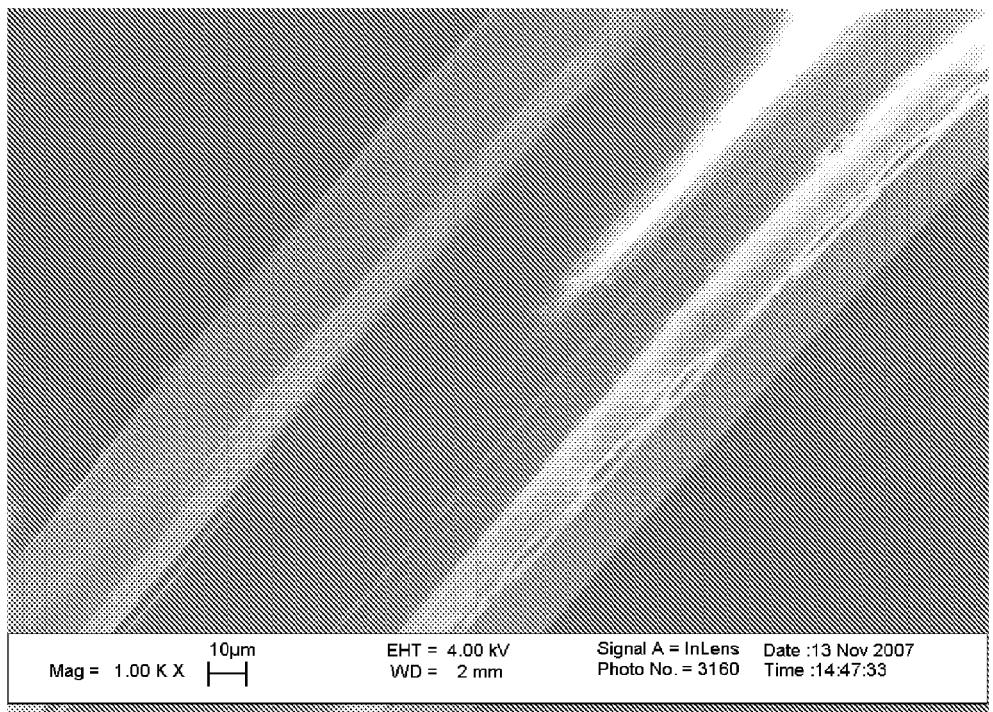
Figure 15:
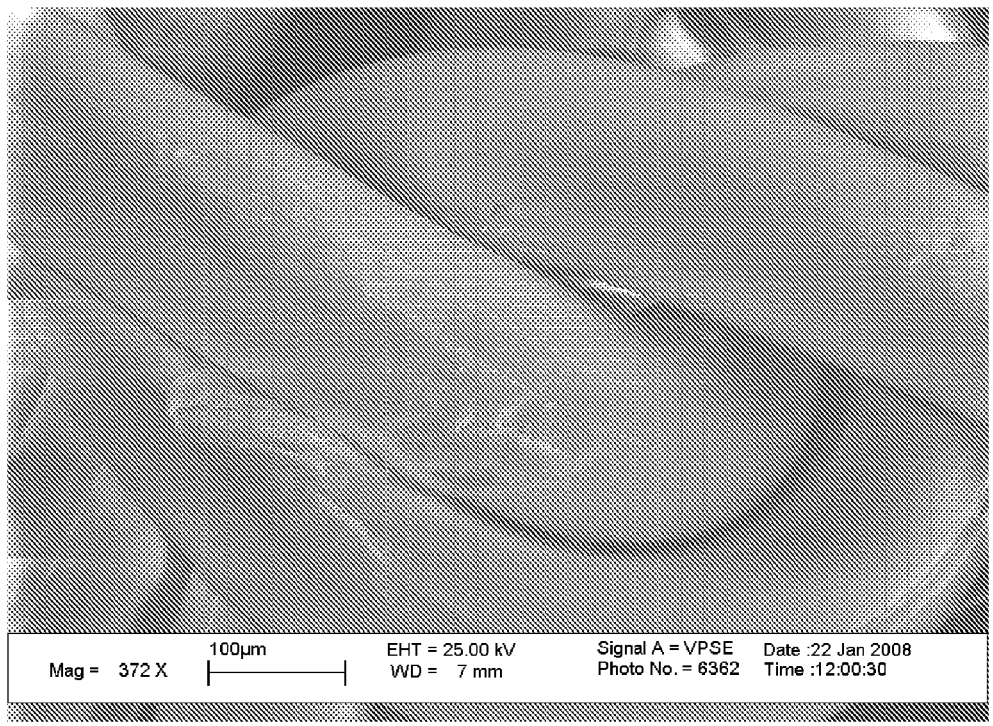

As shown in the SEM image of FIG. 15, the control (untreated) surface of polypropylene (A) is smooth relative to the nano-rough surface morphology of polypropylene (B) treated using a protocol similar to that described in Example 1. As also shown in the SEM image of FIG. 15, the control (untreated) surface of polypropylene mesh fibers (C) is smooth relative to the nano-rough surface morphology of polypropylene mesh fibers (D) treated using a protocol similar to that described in Example 1.

Figure 16:
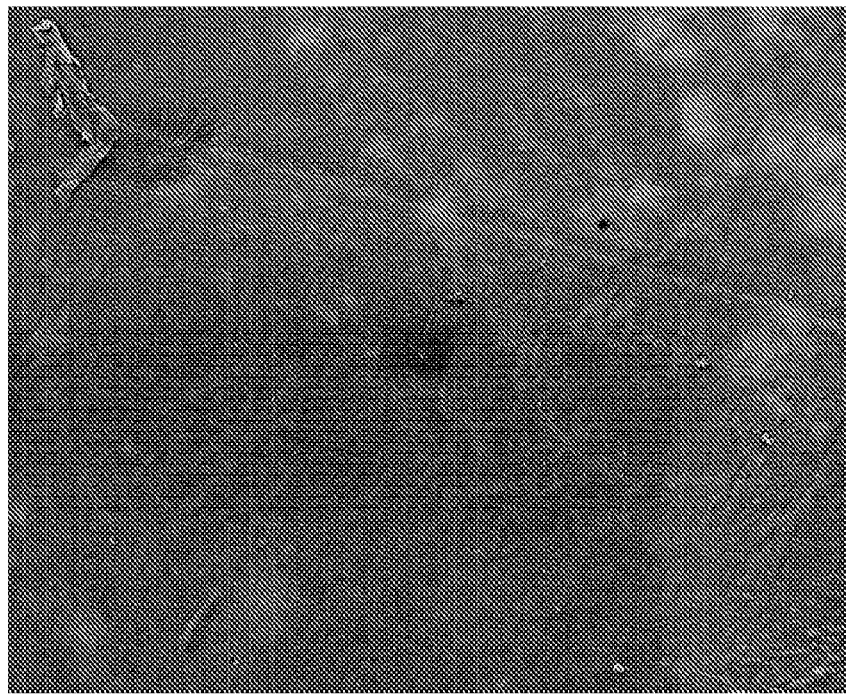
FIG. 16 is an image of the surface morphology of untreated polyvinyl chloride (A) and nano-structured polyvinyl chloride (B).
Figure 16:
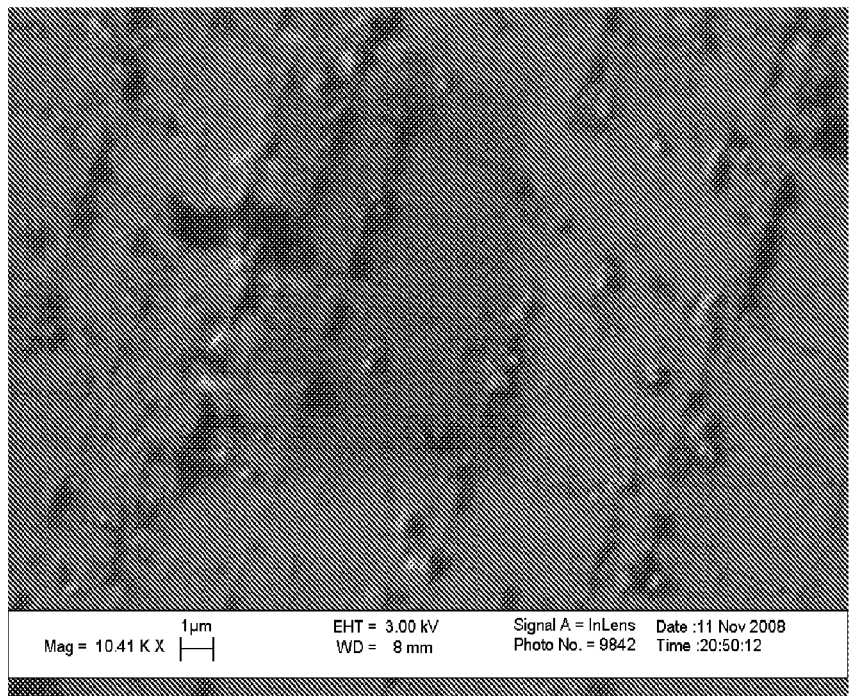

As shown in the SEM image of FIG. 16, the control (untreated) surface of polyvinyl chloride (A) is smooth relative to the nano-rough surface morphology of polyvinyl chloride (B) treated using a protocol similar to that described in Example 1.

Figure 17:
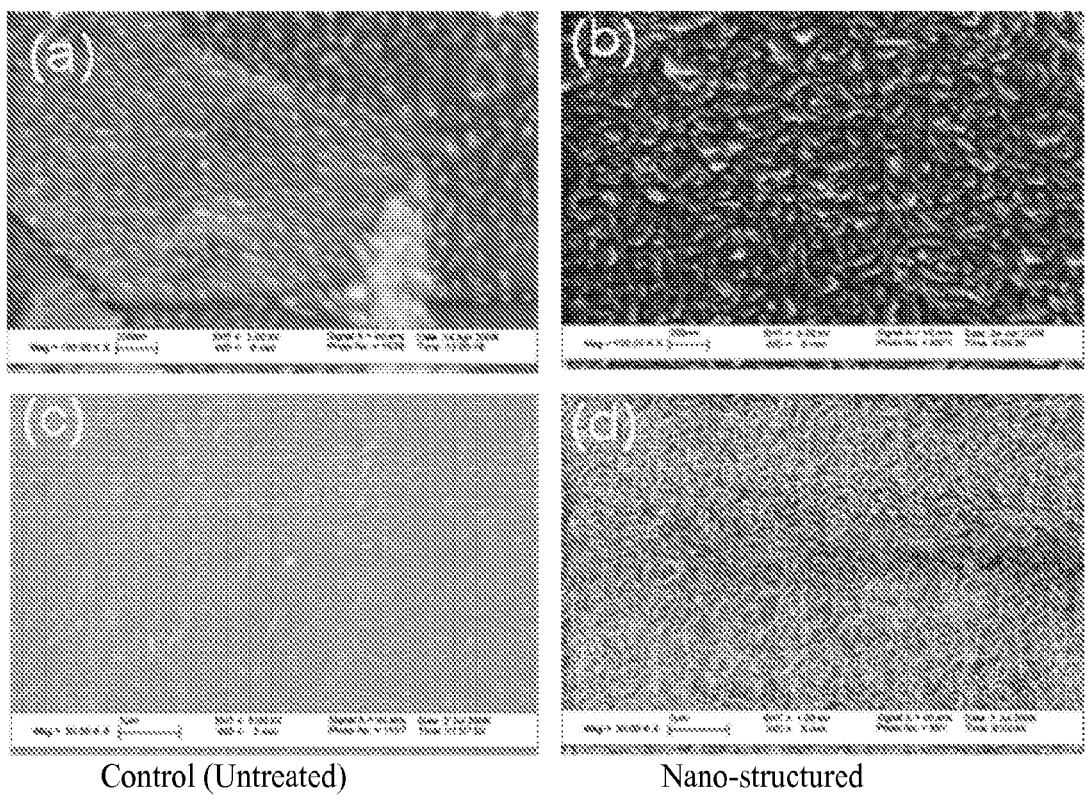
FIG. 17 is an image of the surface morphology of untreated polyethylene (a) and (c) and nano-structured polyvinyl chloride (b) and (d).

As shown in the SEM image of FIG. 17, the control (untreated) surface of polyethylene (A) and (C) is smooth relative to the nano-rough surface morphology of polyethylene (B) and (D) treated using a protocol similar to that described in Example 1.

Figure 18:
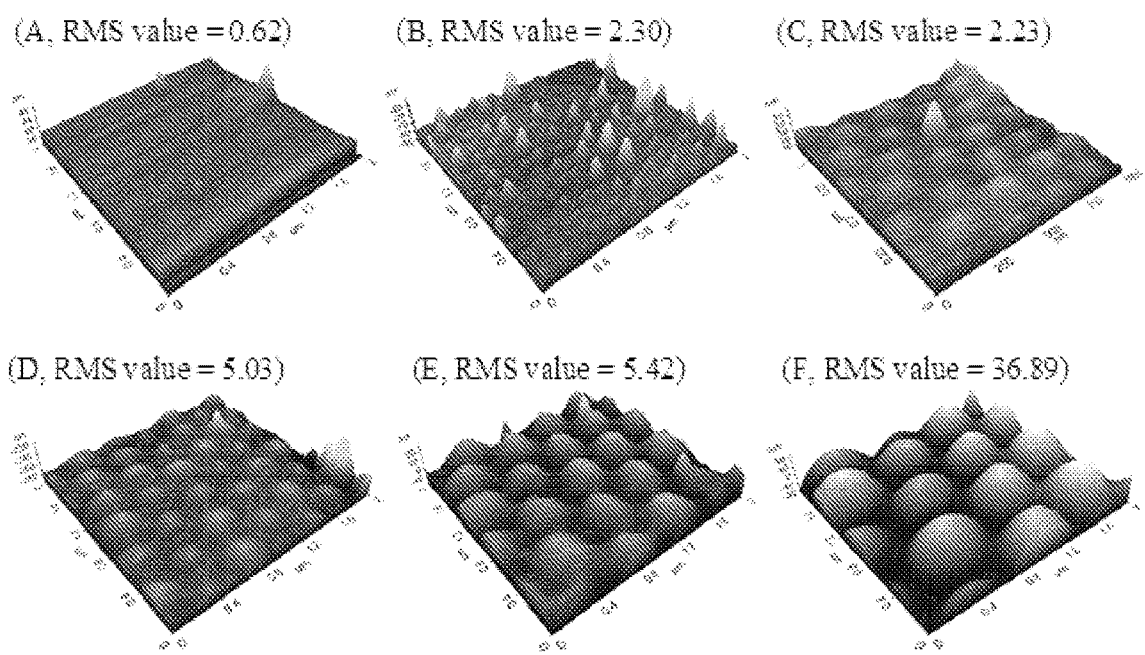
FIG. 18 are AFM images of a silicone substrate with various nano-structured surfaces.

As shown in the AFM images of FIG. 18, silicone has been rendered nano-structured according to the methods of the present disclosure using a protocol similar to that described in Example 1. The first image is a control with no surface treatment and accordingly no nanoscale roughness. The remaining images with surface treatment show various nanoscale surface features.

Example 9

Nanostructured Medical Devices

Figure 19:
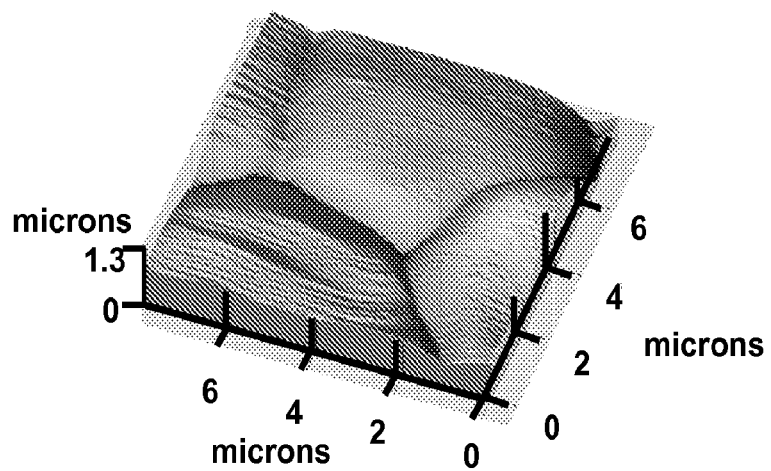
FIG. 19 is a depiction of the surface morphology of an untreated medical device and a medical device have a surface treated to produce a nano-structured surface.
Figure 19:
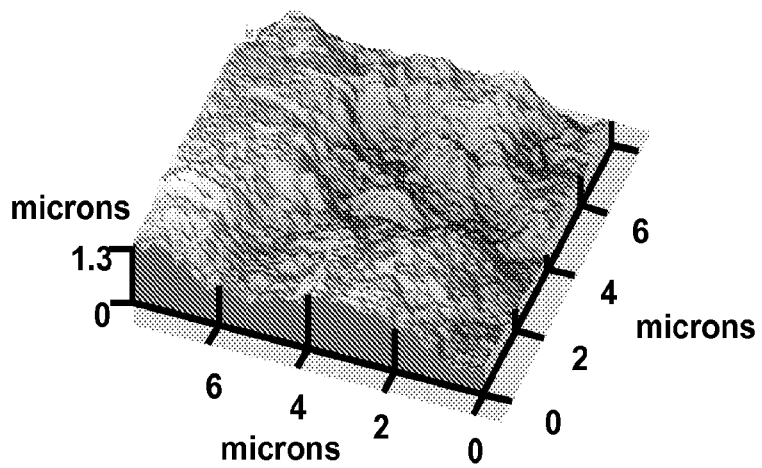

FIG. 19 is an image of the relative surface morphology of the untreated titania surface of a medical device and the titania surface of a medical device treated to have nanoscale surface features through the compaction of titania nanoparticles. Specifically, titania nanoparticles (23 nm diameter) obtained from Nanophase Technologies, Inc. were pressed in a serial dye at 1 GPa of pressure over 10 minutes to form a compact with nanoscale features (bottom). The top image is the roughness of a standard hip implant which shows a lack of nanometer surface features. The nanostructured surface inhibits the attachment, growth and/or differentiation of bacterial cells.

Example 10

Decreased *Pseudomonas aeruginosa* Growth on Nanostructured Surfaces

The effect of a nanostructured surface on the growth of *Pseudomonas aeruginosa* was determined as follows. Commercially available Sheridan® 6.0 mm ID, uncuffed endotracheal tubes (ETTs) (Hudson RIC, Temecula, Calif.) were cut vertically into 0.6 cm by 0.3 cm segments using a rectangular hole punch. To create a nanorough (Nano-R) topography on the PVC, a lipase from *Rhizopus arrhizus* (Sigma-Aldrich, St. Louis, Mo.) was used at a 0.1% concentration in a 1M potassium phosphate buffer. The PVC samples were soaked in the *Rhizopus arrhizus* solution at 37° C., 200 rpm for 24 h. After 24 h, the solution was replaced with fresh solution and the samples were soaked for an additional 24 h. Upon completion of the enzymatic treatment, the Nano-R samples were removed and rinsed three times with double distilled water. The samples were then removed and dried overnight at room temperature. When the Nano-R samples were completely dry, they were sterilized using ethylene oxide gas. Untreated PVC samples were also sterilized using ethylene oxide gas prior to experimentation.

Figure 20:
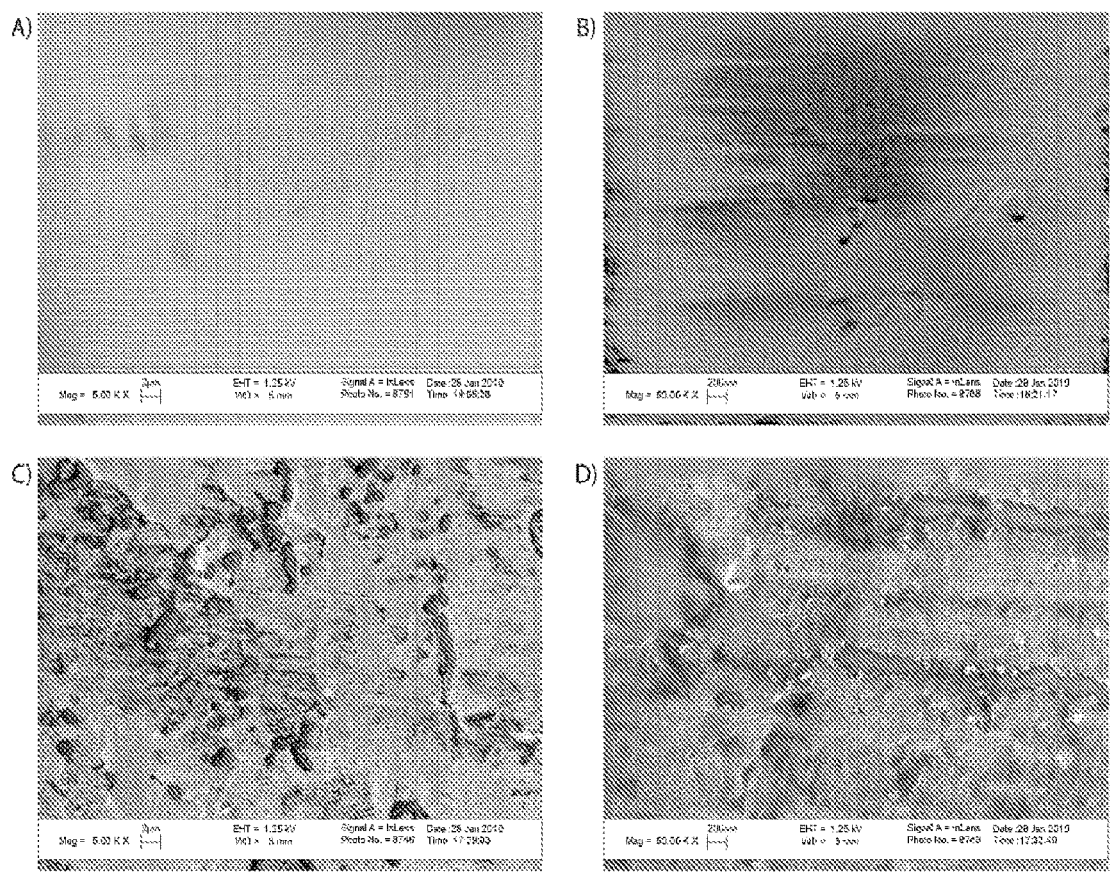
FIG. 20 are SEM images of untreated polyvinyl chloride (A) and (B) and polyvinyl chloride treated with *R. arrhisus* to produce a nano-structured surface (C) and (D).

Surface topography of the material was visualized using a scanning electron microscope (LEO 1530VP FE-4800 Field-Emission SEM, Carl Zeiss SMT, Inc. Peabody, Mass.) according to standard operating procedure. Samples were mounted on aluminum stubs, sputter coated to provide a conductive gold/palladium coating with a thickness of 90 Å, and imaged with an accelerating voltage of 0.5 to 2 kV. As shown in FIG. 20, SEM images of untreated PVC at 5 K× magnification (A) and 50 K× magnification (B) revealed a surface topography that is smooth at the nanoscale. Images of Nano-R surfaces at 5K× magnification (C) and 50K× magnification (D) show a nanorough topography revealing surface degradation of the PVC.

Figure 21:
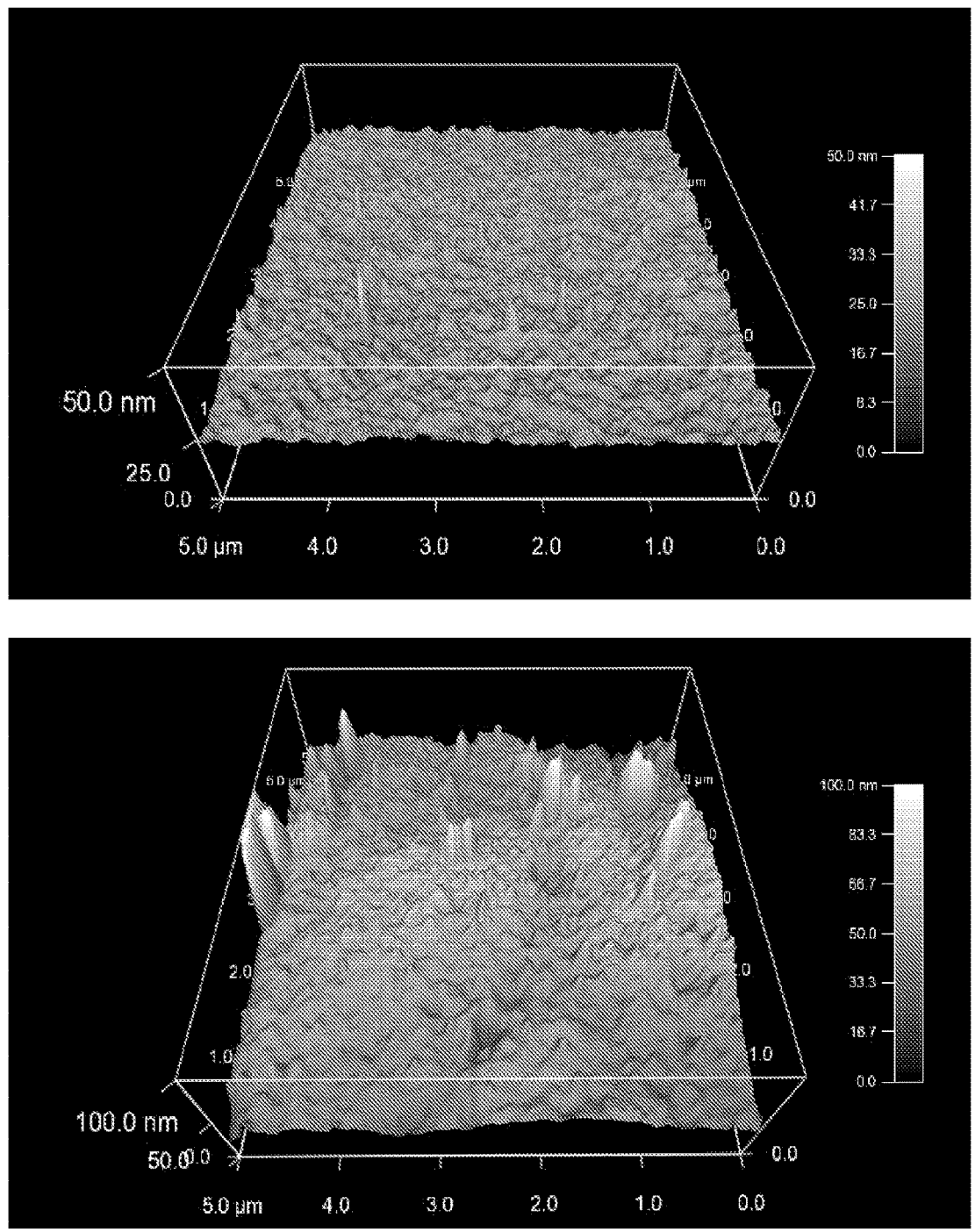
FIG. 21 are AFM images of untreated polyvinyl chloride (A) and polyvinyl chloride treated with *R. arrhisus* to produce a nano-structured surface (B).

The topography of the PVC substrates were evaluated with atomic force microscopy (AFM: XE-100, Park Systems Inc, Santa Clara, Calif.) under tapping mode using a 10 nm AFM tip (PPP-NCHR, Park Systems Inc, Santa Clara, Calif.) with a scan rate of 0.5 Hz. As shown in FIG. 21, AFM images and results for untreated PVC (top) and Nano-R PVC (bottom) indicated RMS values of 2.155±0.7955 nm for untreated PVC and 45.298±18.785 nm for Nano-R PVC.

Figure 22:
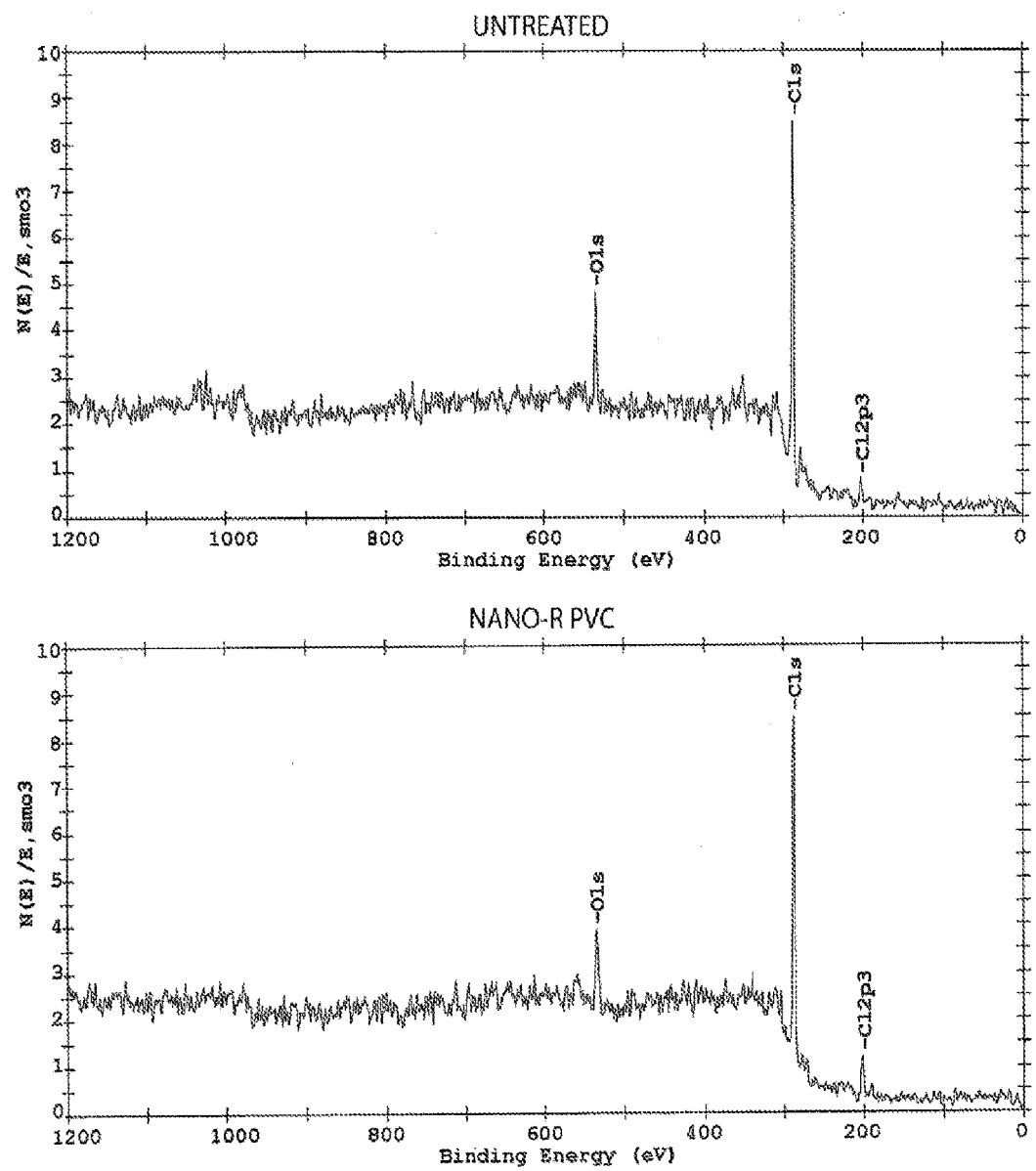
FIG. 22 are XPS graphs of untreated polyvinyl chloride (top) and polyvinyl chloride treated with *R. arrhisus* to produce a nano-structured surface (bottom) showing carbon and chlorine peaks indicating that the creation of a nano-structured surface did not alter material chemistry.

To compare the surface chemistry of the treated and untreated PVC samples, X-ray photoelectron spectroscopy (XPS) analysis was used. A brief sputter cleaning was performed to eliminate surface contamination. Parameters of the XPS system (5500 Multitechnique Surface Analyzer, Perkin Elmer, Waltham, Mass.) were adjusted to analyze the top 50 Å of the material surface over a circular area with a diameter of 1.1 mm. Acquired data was processed with appropriate software (PC Access ESCA V7.2C, Physical Electronics, Chanhassen, Minn.). As shown in FIG. 22, XPS data of untreated PVC (top) and Nano-R PVC (bottom) revealed carbon and chlorine peaks indicative of PVC. Matching peaks indicated that the creation of Nano-R topography did not alter material chemistry.

*Pseudomonas aeruginosa* (ATCC 25668, American Type Culture Collection, Manassas, Va.) was hydrated and streaked for isolation on a tryptic soy agar plate. Following growth, a single isolated colony was selected and used to inoculate 5 ml of tryptic soy broth (TSB). The bacteria culture was grown on an incubator shaker for 18 hours at 37° C., 200 rpm. The bacteria suspension was diluted 1:30, and 150 µl of the bacteria culture was added to a single well of a round bottom, non-tissue treated 96 well plate containing either a Nano-R or an untreated PVC sample. The plate was then placed in a stationary incubator at 37° C. with 5% carbon dioxide. After 24 hours, the plate was removed, and the excess media was carefully aspirated. Media residue and non-adherent bacteria were carefully rinsed from sample surfaces with phosphate buffered saline (PBS). Following the removal of the PBS, the PVC samples were extracted from the well plates using a pair of sterile forceps. Samples were gently removed and an effort was made to minimize forcep contact that could disrupt biofilms on the surfaces. Each sample was then placed into a 20 mL disposable scintillation vial containing 2 ml of TSB for further mechanical stimulation to remove biofilm. An additional control vial received no additives or mechanical stimulation. Samples were kept at room temperature from the time of sample transfer to the scintillation vials until processing within 30 min according to one of the four methods described below.

Biofilm Removal Process 1: The vial containing the PVC sample was vortexed for 1 min at 3000 rpm. The degree of turbulence in the media in the scintillation vial depended on the angle at which the vial was held onto the vortex. The firmness with which the vial was held also affected the apparent degree of turbulence. For consistency, the vials were held in a vertical position with a slightly softened grip. Proper vortexing was indicated by the appearance of media swirling around the circumference of the vial from top to bottom.

Biofilm Removal Process 2: The vial containing the PVC sample was placed in a tabletop ultrasonic cleaner (B3500A, VWR International, Batavia, Ill.) and sonicated for 10 min at the highest setting. The output of the ultrasonic cleaner, which contained 5.7 L of water, was 135 W at a frequency of 42 kHz.

Biofilm Removal Process 3: The vial containing the PVC sample was vortexed for 1 min at 3000 rpm as described above, and then sonicated for 10 min on the highest setting as described above.

Biofilm Removal Process 4: The vial containing the PVC sample includes TWEEN 80 in the TSB (5% by volume). The vial was vortexed for 1 min at 3000 rpm.

Figure 23:
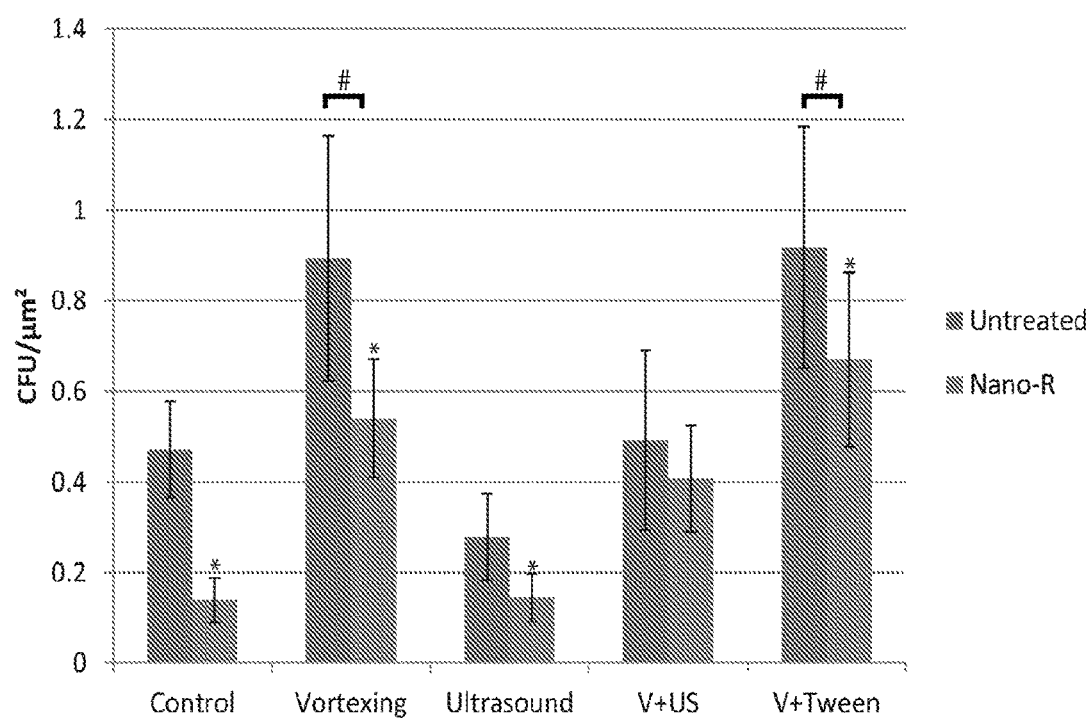
FIG. 23 is a graph of colony forming units (CFU) of *Pseudomonas aeruginosa* removed using various methods from untreated polyvinyl chloride and polyvinyl chloride treated with *R. arrhisus* to produce a nano-structured surface.

Following each of the four treatments described above, the supernatant media was serially diluted and plated on tryptic soy agar plates to quantify the number of viable cells removed from the surfaces. For all experimental and control groups, the $10^{-5}$ dilution plating provided colony numbers in a countable range. Colony forming units (CFU) of *Pseudomonas aeruginosa* were counted via a spread plate technique after an overnight incubation. As shown in FIG. 23, all methods of removal (with the exception of vortexing plus ultrasound [V+US]) showed a greater *Pseudomonas* population on untreated samples compared to Nano-R PVC, with vortexing providing high CFU yield. Values are mean±SEM; N=3; *$p<0.05$ (compared to untreated samples under same conditions), #$p<0.05$ (for both untreated and Nano-R compared to control). This demonstrates a reduced presence of bacteria on the Nano-R PVC achieved without the use of antimicrobial agents. Numerical data were analyzed for significance using the student's t-test (N=3). Experiments were performed in triplicate. Values are reported as the mean±SEM. The threshold for significance was set at $p<0.05$.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed is:

1. A method of reducing growth of bacteria on a surface of a polyvinyl chloride substrate comprising:
    altering the surface of the polyvinyl chloride substrate to produce a nanometer scale surface geometry by:
        contacting the surface of the polyvinyl chloride substrate with a solution of a nano-roughing agent to produce a nanometer scale surface geometry on the surface of the substrate, and
    contacting the surface with bacteria, wherein growth of the bacteria on the altered polyvinyl chloride surface is inhibited by about 30% to about 50%, as measured by contacting the altered polyvinyl chloride surface with *Staphylococcus aureus* bacteria for 4 to 72 hours as compared to contacting the untreated polyvinyl chloride surface with *Staphylococcus aureus* bacteria for 4 to 72 hours.

2. The method of claim 1 wherein the nano-roughing agent is one or more of an acid, a base, a bacterial lipase, an alcohol, a peroxide, isoamyl acetate, dichloromethane, isoamyl acetate with zinc, dichloromethane with zinc, acetic acid, sulfuric acid, nitric acid, perchloric acid, phosphoric acid, hydrochloric acid, chloroform, acetone, ethanol, ammonia, sodium hydroxide, potassium hydroxide, ammonium hydroxide, ammonium fluoride, hydrofluoric acid, triflic acid, hydrogen peroxide, dichloroethylene, or xylene.

3. The method of claim 1 wherein the nano-roughing agent is one or more of phospholipases, sphingomyelinases, hepatic lipase, endothelial lipase, lipoprotein lipase, bile salt dependent lipase, pancreatic lipase, lysosomal lipase, hormone-sensitive lipase, gastric lipase, pancreatic lipase related protein 2, pancreatic lipase related protein 1, lingual lipase, and bacterial lipase produced from one or more of *Rhisopus arrhisus, Candida cilindracea, Candida rugosa, Thermus thermophilus, Candida Antarctica, Aspergillus niger, Aspergillus oryzae, Aspergillus sp, Burkholderia sp, Candida utilis, Chromobacterium viscosum, Mucor javanicus, Penicillium roqueforti,* or *Pseudomonas cepacia*.

4. The method of claim 1 wherein the surface of the substrate is contacted with a solution of *Rhisopus arrhisus* or *Candida cilindracea*.

5. The method of claim 1 wherein the substrate further includes a metal, wherein the metal is one or more of titanium, aluminum, platinum, niobium, tantalum, tin, nickel, cobalt, chromium, molybdenum, stainless steel, nitinol, SiN, CoCrMo, or mixtures or alloys thereof.

6. The method of claim 1 wherein the substrate further includes a ceramic, wherein the ceramic is one or more of alumina, hydroxyapatite, silica, calcium phosphates, or bone cements, or composites thereof.

7. The method of claim 1 wherein the substrate is an endotracheal tube.

8. The method of claim 1 wherein the bacteria is one or more of *Staphylococcus aureus, Staphylococcus epidermis, Pseudomonas aeruginosa,* MRSA, *E. coli,* candida (yeast), *Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium,* tuberculosis, *Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium,* Enterobacteriaceae, or *Staphylococcus saprophyticus.*

9. The method of claim 1, wherein the surface of the substrate includes a metal, wherein the metal is one or more of platinum, tin, molybdenum, stainless steel, SiN, or mixtures or alloys thereof.

10. The method of claim 1, wherein the surface of the substrate includes a ceramic, wherein the ceramic is one or more of alumina, silica, calcium phosphates, or bone cements, or composites thereof.

\* \* \* \* \*